US012655475B2

(12) United States Patent
Zhang et al.

(10) Patent No.: US 12,655,475 B2
(45) Date of Patent: Jun. 16, 2026

(54) MICROFLUIDIC NUCLEIC ACID DETECTION KIT AND DETECTION DEVICE

(71) Applicant: CHENGDU ONE-CHIP BIOTECHNOLOGY CO., LTD., Chengdu (CN)

(72) Inventors: Zhifeng Zhang, Chengdu (CN); Jianlong Li, Chengdu (CN)

(73) Assignee: CHENGDU ONE-CHIP BIOTECHNOLOGY CO., LTD., Chengdu (CN)

( * ) Notice: Subject to any disclaimer, the term of this patent is extended or adjusted under 35 U.S.C. 154(b) by 795 days.

(21) Appl. No.: 18/020,948

(22) PCT Filed: May 10, 2022

(86) PCT No.: PCT/CN2022/091872
§ 371 (c)(1),
(2) Date: Feb. 13, 2023

(87) PCT Pub. No.: WO2022/242499
PCT Pub. Date: Nov. 24, 2022

(65) Prior Publication Data
US 2023/0295700 A1     Sep. 21, 2023

(30) Foreign Application Priority Data

May 18, 2021   (CN) .......................... 202110540815.9
Apr. 14, 2022   (CN) .......................... 202210387718.5

(51) Int. Cl.
*B01L 3/00*          (2006.01)
*B01L 7/00*          (2006.01)
*C12Q 1/6844*      (2018.01)
(52) U.S. Cl.
CPC ...... *C12Q 1/6844* (2013.01); *B01L 3/502715* (2013.01); *B01L 2200/04* (2013.01);
(Continued)

(58) Field of Classification Search
None
See application file for complete search history.

(56) References Cited

U.S. PATENT DOCUMENTS

| | | | |
|---|---|---|---|
| 2016/0175835 A1 | 6/2016 | Taylor et al. | |
| 2018/0243739 A1 | 8/2018 | Schenk zu Schweinsberg et al. | |
| 2019/0336972 A1 | 11/2019 | Gutsell | |

FOREIGN PATENT DOCUMENTS

| | | |
|---|---|---|
| AU | 2019237517 A1 | 3/2024 |
| CN | 110257245 A | 9/2019 |

(Continued)

OTHER PUBLICATIONS

CN 113897283 A English Translation (Year: 2022).*

*Primary Examiner* — Brittany I Fisher
(74) *Attorney, Agent, or Firm* — Bayramoglu Law Offices LLC

(57)          ABSTRACT

A microfluidic nucleic acid detection kit and a detection device are provided. The microfluidic nucleic acid detection kit is provided includes a kit body and a reagent card interconnected. The kit body can slide relative to the reagent card to control the kit to work. The microfluidic nucleic acid detection kit further includes a gas source cavity, a liquid cavity, a nucleic acid amplification cavity, and a gas tail cavity. The gas tail cavity communicates with the nucleic acid amplification cavity through an exhaust gas flow channel. The exhaust gas flow channel is provided with a check valve. The detection device includes the microfluidic nucleic acid detection kit, a first housing, a power module, a display module, a first heating module, and a first detection module. The microfluidic nucleic acid detection kit is removably inserted into the first housing.

32 Claims, 13 Drawing Sheets

(52) U.S. Cl.
CPC ..... *B01L 2200/16* (2013.01); *B01L 2300/027*
(2013.01); *B01L 2300/0877* (2013.01); *B01L*
*2400/0487* (2013.01); *B01L 2400/0622*
(2013.01)

(56) References Cited

FOREIGN PATENT DOCUMENTS

| | | | |
|----|-------------|---|---------|
| CN | 110331089   | A | 10/2019 |
| CN | 111269826   | A | 6/2020  |
| CN | 111704993   | A | 9/2020  |
| CN | 112300927   | A | 2/2021  |
| CN | 113897283   | A | 1/2022  |
| JP | 2016052253  | A | 4/2016  |

* cited by examiner

21

212

2133
2132
21311
213
2131

211

13

21

18

11

12

10

52

525

522

524

521

523

521

6

61

64

63

MICROFLUIDIC NUCLEIC ACID DETECTION KIT AND DETECTION DEVICE

CROSS REFERENCE TO THE RELATED APPLICATIONS

This application is the national phase entry of International Application No. PCT/CN2022/091872, filed on May 10, 2022, which is based upon and claims priority to Chinese Patent Application No. 202110540815.9, filed on May 18, 2021, and No. 202210387718.5, filed on Apr. 14, 2022, the entire contents of which are incorporated herein by reference.

TECHNICAL FIELD

The present disclosure relates to the field of in vitro diagnosis (IVD) equipment and in particular to a microfluidic nucleic acid detection kit and a detection device for a point-of-care testing (POCT) scenario.

BACKGROUND

The IVD technology refers to a product and service by which relevant clinical diagnostic information can be acquired through in vitro detection of samples including blood, bodily fluids, and tissues of the body to help determine a disease or a body function. The IVD field involves an extremely-broad scope, including blood tests, clinical biochemistry, cytodiagnosis, microbiological diagnosis, coagulation diagnosis, immunochemistry, molecular diagnosis, POCT, and the like. Currently, IVD, which has great development potential and fast growth, refers to molecular diagnosis and POCT that are mainly based on nucleic acid detection.

With the social progress, there is an increasing demand for low-cost and safe POCT diagnostic equipment that can be used outside the laboratory, such as in community hospitals, drugstores, and homes. At present, most nucleic acid detection kits on the market cannot be used outside a professional biological laboratory. Sample processing using these kits should not be exposed to contamination and thus must be completed in a laboratory, and the entire process of detection requires various professional devices to complete the lysis of a biological sample, the extraction of nucleic acid, the PCR amplification of nucleic acid, the acquisition of an optical signal, and the data analysis.

In recent years, with technological progress, advanced integrated and fully-automated nucleic acid detection POCT kits and supporting devices thereof have gradually been developed in the industry, such as the Xpert® product of Cypheid in the United States, the FilmArray® product of BioFire in France, and the Vivalytic product of Bosch in Germany. External power is required for these products to operate the components in the kits to control various liquid flows in the kits, thereby achieving the automation of the whole process of lysis, extraction, amplification, and detection of a nucleic acid sample. However, these products involve expensive detection instruments and reagent cards, and the detection instruments are still complicated and bulky and are not portable. In addition, most of these products still need to be used in a special PCR laboratory and cannot be used for a POCT application scenario. Some POCT kits adopt the constant-temperature amplification technology and the one-step nucleic acid lysis and extraction technology to greatly simplify reagent cards and detection instruments and even realize home nucleic acid detectors. For example, the home nucleic acid detection products of Lucira™ in the United States realize the sample extraction and amplification in a kit without relying on the external equipment. However, to achieve accurate liquid flow and control, it is necessary to leave a gas outlet on a kit to achieve the liquid control, and a filter membrane is optionally arranged at the gas outlet to prevent aerosol pollution, but the filter membrane cannot completely prevent the overflow of an aerosol. In particular, the loop-mediated isothermal amplification (LAMP) adopted will lead to a high virus concentration in a cavity and possible aerol pollution from the test kit to the environment.

SUMMARY

The present disclosure is intended to provide an integrated and fully-automated POCT microfluidic nucleic acid detection kit and a detection device including the same, which solves the technical problems in the prior art that the existing kits cannot be used for detection completely outside a laboratory, cannot be completely sealed and free of nucleic acid contamination, and lead to complicated equipment systems due to the use of external power.

As conceived above, a first aspect of the present disclosure provides the following technical solution:

A microfluidic nucleic acid detection kit is provided, including a kit body and a reagent card that are interconnected, where the kit body can slide relative to the reagent card to control the kit to work. The microfluidic nucleic acid detection kit further includes a plurality of cavities and a plurality of flow channels that communicate with the plurality of cavities. The plurality of cavities and the plurality of flow channels form a closed system. The plurality of cavities at least includes:

a gas source cavity arranged in the kit body and capable of controlling the gas pressure of the closed system through a volume change;

a liquid cavity arranged in the kit body and configured to inject a liquid reagent, where the liquid cavity communicates with the gas source cavity through a gas source flow channel;

a nucleic acid amplification cavity arranged on the reagent card, where the nucleic acid amplification cavity communicates with the liquid cavity through a sample injection flow channel; a gas tail cavity arranged on the reagent card, where the gas tail cavity communicates with the nucleic acid amplification cavity through an exhaust gas flow channel. A first sealing membrane is arranged on the reagent card, where the first sealing membrane seals the sample injection flow channel, the exhaust gas flow channel, and the gas tail cavity.

Further, a check valve is provided at the exhaust gas flow channel, and the check valve is configured to block the circulation of a liquid and discharge gas.

Further, the plurality of cavities further includes a bubble storage cavity, the bubble storage cavity is arranged between the exhaust gas flow channel and the nucleic acid amplification cavity, and the bubble storage cavity communicates with the nucleic acid amplification cavity.

Further, the kit body and the reagent card are connected through a buckle assembly; the buckle assembly includes a buckle fastener arranged on the reagent card and a bayonet buckle arranged on the kit body.

The buckle fastener includes a buckle strip. One end of the buckle strip is connected with the reagent card, and the other end of the buckle strip is a free end that extends toward the kit body along the buckle strip. The buckle strip is provided with a first cantilever, and the reagent card is provided with a second cantilever. The second cantilever is located above the first cantilever. The bayonet buckle includes a first bayonet corresponding to the first cantilever and a second bayonet corresponding to the second cantilever.

Further, before the kit body slides relative to the reagent card, both the first cantilever and the second cantilever abut against the kit body, the gas source cavity and the gas tail cavity have the same gas pressure, and the liquid in the liquid cavity does not flow into the nucleic acid amplification cavity.

When the kit body slides relative to the reagent card, the gas source cavity is squeezed, and gas pressure in the gas source cavity increases to push the liquid reagent in the liquid cavity to be injected through the sample injection flow channel into the nucleic acid amplification cavity. The flow of the liquid reagent pushes gas in the nucleic acid amplification cavity to be injected into the gas tail cavity, and the liquid reagent in the liquid cavity stops flowing when reaching the check valve, such that the liquid reagent is accurately injected into the nucleic acid amplification cavity.

Further, a solid reagent required for nucleic acid amplification is placed in the nucleic acid amplification cavity, and the solid reagent includes a dry powder reagent, a lyophilized pellet for a reagent, or an internal standard reagent for quality control (QC). A nucleic acid lysis extract is placed in the liquid cavity with a space reserved for sample addition, and the nucleic acid lysis extract has a volume of 100 μL to 5,000 μL.

Further, a main flow channel is provided between the nucleic acid amplification cavity and the sample injection flow channel, and a wax column is provided between the sample injection flow channel and the main flow channel. When the kit body slides relative to the reagent card, the wax column is melted by a heating device, such that the sample injection flow channel communicates with the main flow channel.

Further, the plurality of cavities further includes a QC internal standard cavity arranged in the kit body. A first lyophilized pellet is placed in the QC internal standard cavity, and the first lyophilized pellet includes a reagent component required for internal QC.

Further, a second lyophilized pellet or a lyophilized powder is placed in the nucleic acid amplification cavity, and the second lyophilized pellet or the lyophilized powder includes a reagent component required for nucleic acid amplification.

Further, the nucleic acid amplification cavity, the check valve, and the gas tail cavity are provided in the same number and correspond to each other.

Further, the bottom of the QC internal standard cavity is inclined at a specified angle with a horizontal plane, and a first lyophilized pellet outlet is formed at the lowest position of the bottom of the QC internal standard cavity.

Further, an end of the sample injection flow channel close to the liquid cavity is provided with a puncture needle. The puncture needle is able to be inserted into the liquid cavity, such that the puncture needle extends into the liquid cavity to make the sample injection flow channel communicate with the liquid cavity.

Further, the reagent card is provided with a piston rod, and the end of the piston rod is provided with a rubber piston.

The gas source cavity is shaped like a blind hole on the kit body. The end of the piston rod provided with the rubber piston extends into a blind end of the gas source cavity through an open end of the gas source cavity, and the gas source flow channel is arranged near the blind end of the gas source cavity.

Before the kit body slides relative to the reagent card, the rubber piston is located in the gas source cavity at a position lower than the gas source flow channel.

When the kit body slides relative to the reagent card, the rubber piston moves toward the blind end to feed gas from the gas source cavity into the liquid cavity.

Further, a sample injection port is formed on the kit body, and the sample injection port is in communication with the liquid cavity. The sample injection port is formed at the end of the liquid cavity away from the sample injection flow channel. A first lyophilized pellet inlet and a first lyophilized pellet outlet are formed in the QC internal standard cavity, and the first lyophilized pellet outlet communicates with the liquid cavity and the QC internal standard cavity.

Further, the kit body further includes an upper cover. The upper cover is provided with a protrusion to seal the sample injection port and the first lyophilized pellet outlet, and the upper cover can cover the first lyophilized pellet inlet.

Further, the end of the liquid cavity away from the sample injection port is provided with a second sealing membrane, and the puncture needle can be inserted into the liquid cavity such that the end of the puncture needle penetrates through the second sealing membrane and communicates with the liquid cavity. A third sealing membrane is provided at the first lyophilized pellet inlet, and a fourth sealing membrane is provided at the first lyophilized pellet outlet.

The fourth sealing membrane includes a first portion, a second portion, and a third portion that are integrally formed. The first portion seals the first lyophilized pellet outlet, the second portion seals the liquid cavity, and the third portion is a ring-pull structure that is able to extend out of the sample injection port.

Further, the sample injection flow channel tapers from the end away from the main flow channel to the end close to the main flow channel.

In a first aspect of the present disclosure, a nucleic acid detection kit is provided. Because the whole process of the kit body sliding relative to the reagent card is implemented in the nucleic acid detection kit, there is no need to form a gas outlet in the nucleic acid detection kit, such that the nucleic acid detection kit can be fully sealed and used completely outside the laboratory without pollution. In addition, the nucleic acid detection kit can work without external power and involves simple detection devices. The fully sealing is conceived by the inventors based on the principle that a gas can be compressed while a liquid cannot be compressed. Before the kit body slides relative to the reagent card, the gas source cavity and the gas tail cavity have the same gas pressure and the second sealing membrane is not punctured, such that the liquid in the liquid cavity will not flow into the nucleic acid amplification cavity. When the kit body slides relative to the reagent card, the gas source cavity is compressed, and gas pressure in the gas source cavity increases to push a liquid reagent in the liquid cavity to be injected through the sample injection flow channel into the nucleic acid amplification cavity. The flow of the liquid reagent pushes gas in the nucleic acid amplification cavity to be injected into the gas tail cavity, and the liquid reagent in the liquid cavity stops flowing when the check valve is reached, such that the liquid reagent is accurately injected into the nucleic acid amplification cavity.

A second aspect of the present disclosure provides the following technical solution:

A detection device is provided, including the microfluidic nucleic acid detection kit described above, a first housing, a power module, and a display module, where the microfluidic nucleic acid detection kit is removably inserted into the first housing. The detection device further includes:

a first heating module configured to heat the nucleic acid amplification cavity and a first detection module arranged in the first housing and configured to detect a change of an optical signal in the nucleic acid amplification cavity. The optical signal includes one or more selected from the group consisting of color, brightness, fluorescence, and saturation signals.

Further, the detection device further includes: a first circuit board arranged in the first housing and a control unit arranged on the first circuit board. The control unit is electrically connected with the first heating module to control the first heating module to heat the nucleic acid amplification cavity.

Further, the first heating module includes a heating member closely surrounding the nucleic acid amplification cavity, a first heating plate that is arranged at the bottom of the heating member and is in contact with the heating member for heat conduction, and a temperature sensor adjacent to the first heating plate. The temperature sensor is electrically connected to the control unit, and a heat dissipation space is formed between the first heating module and the first circuit board.

Further, a heating groove and first and second holes arranged oppositely are formed in the heating member. The first hole and the second hole both penetrate through the heating groove. The nucleic acid amplification cavity extends into the heating groove and is located between the first hole and the second hole.

Further, the first detection module includes a light source and a light sensor each of which are electrically connected to the first circuit board. The light source and the light sensor both are arranged outside the heating member. The light source is attached to the first hole, and the light sensor is attached to the second hole.

Further, the first circuit board is provided with a processing unit configured to process and analyze an optical signal acquired by the detection module and then feed an analysis result back to the display module.

Further, the processing unit includes a data acquisition circuit, an ADC chip, and a processor. A signal of the light sensor is acquired by the data acquisition circuit, subjected to analog-to-digital conversion by the ADC chip, and transmitted to the processor for processing and analysis of a digital signal, and an analysis result is fed back to the display module to obtain detection data.

Further, the first circuit board is provided with a data communication unit configured to transmit the detection data to a wireless terminal. The wireless terminal includes, but is not limited to, one or more selected from the group consisting of a mobile terminal, a computer, and a network server.

Further, the first housing includes a housing body with an opening formed at an upper end and an upper housing cover that is rotatably connected with the housing body and configured to cover the opening. The nucleic acid detection kit is removably inserted into the opening. A mounting position for arranging the display module is provided on the housing body, and the display module is arranged at the mounting position.

In the detection device provided in the second aspect of the present disclosure, the nucleic acid detection kit is removably inserted into the detection device, and the nucleic acid detection kit is disposable.

The nucleic acid detection device can be used completely outside the laboratory, processes samples and injects and detects samples in a full-sealed manner, and eliminates aerosol pollution and other pollution risks.

A third aspect of the present disclosure adopts the following technical solutions:

An integrated detection device is provided, including the microfluidic nucleic acid detection kit described in the first aspect and a second housing. The integrated detection device further includes:

a second heating module configured to heat the nucleic acid amplification cavity; and a second detection module arranged in the second housing and configured to detect a change of an optical signal in the nucleic acid amplification cavity. The optical signal includes one or more selected from the group consisting of color, brightness, fluorescence, and saturation signals.

Further, the second housing may be integrated or the first housing includes a front cover and a rear cover that are removably connected. The front cover and the rear cover cooperate to hold the microfluidic nucleic acid detection kit, and the second detection module is arranged between the front cover and the rear cover.

Further, the integrated detection device further includes: a second circuit board arranged between the front cover and the rear cover and a control unit arranged on the second circuit board. The control unit is electrically connected with the second heating module to control the second heating module to heat the nucleic acid amplification cavity, and the second circuit board is provided with a power socket.

Further, the second heating module includes a second heating plate closely surrounding the nucleic acid amplification cavity and a temperature sensor that is arranged on the inner surface of the second heating plate and is in contact with the reagent card; the temperature sensor is electrically connected with the control unit.

Further, the second detection module includes a light source and a light guide column both of which are electrically connected to the second circuit board. The light source and the light guide column are respectively located on two sides of the reagent card.

Further, the second circuit board is provided with a processing unit configured to process and analyze an optical signal acquired by the second detection module to obtain detection data.

Further, the processing unit includes a data acquisition circuit, an ADC chip, and a processor. A signal from the light sensor is acquired by the data acquisition circuit, subjected to analog-to-digital conversion by the ADC chip, and transmitted to the processor for processing and analysis of a digital signal to obtain detection data.

Further, the second circuit board is provided with a data communication unit configured to transmit the detection data to a mobile terminal, a computer, a network server, or another wireless terminal.

The present disclosure has the following beneficial effects:

In the integrated detection device provided in the third aspect of the present disclosure, the nucleic acid detection kit and the detection device are integrated to produce an integrated nucleic acid detection device, and the nucleic acid detection kit is disposable and can be changed after one-time detection, which prevents the detection device from contaminating the reagent card. In addition, the integrated nucleic acid detection device can be used completely outside a laboratory, can achieve fully-sealed sample injection and detection, and completely eliminate aerosol pollution and other pollution risks.

Figure 1:
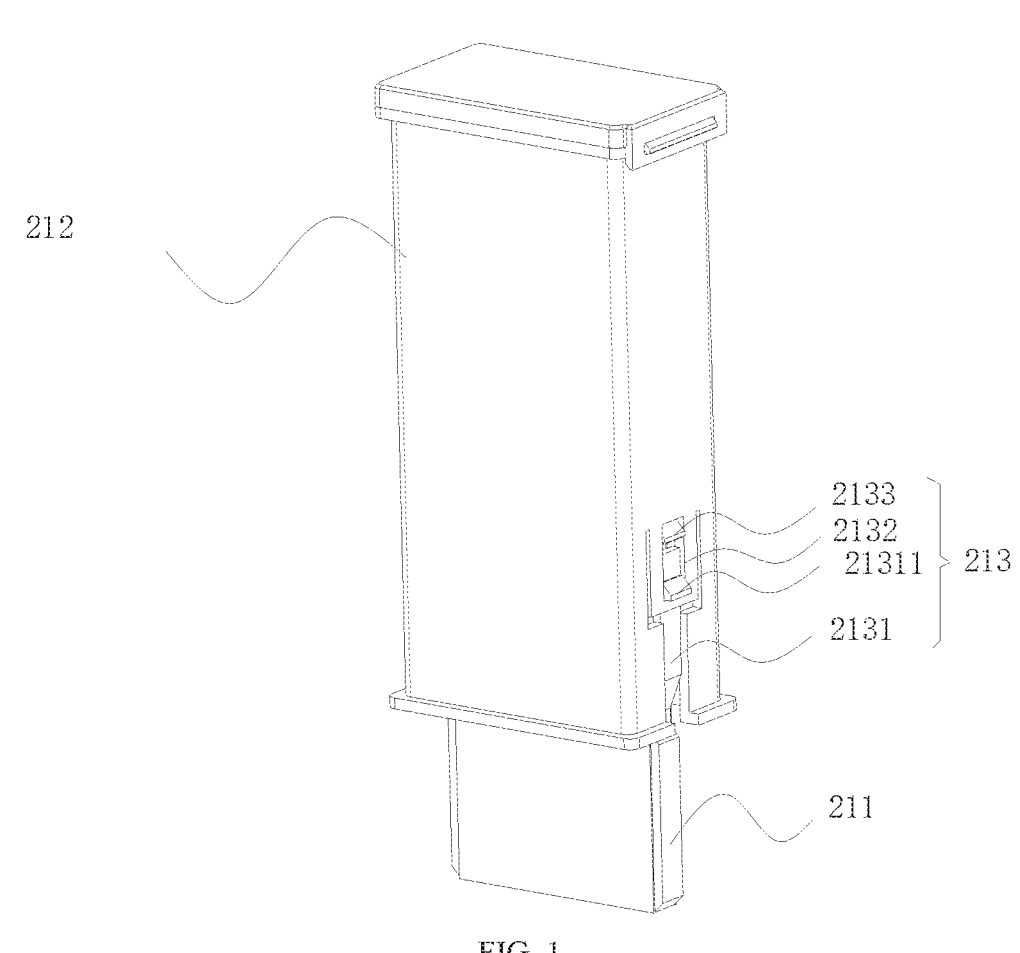
FIG. 1 is a schematic diagram illustrating the structure of the nucleic acid detection kit provided in Example 1 of the present disclosure.
Figure 2:
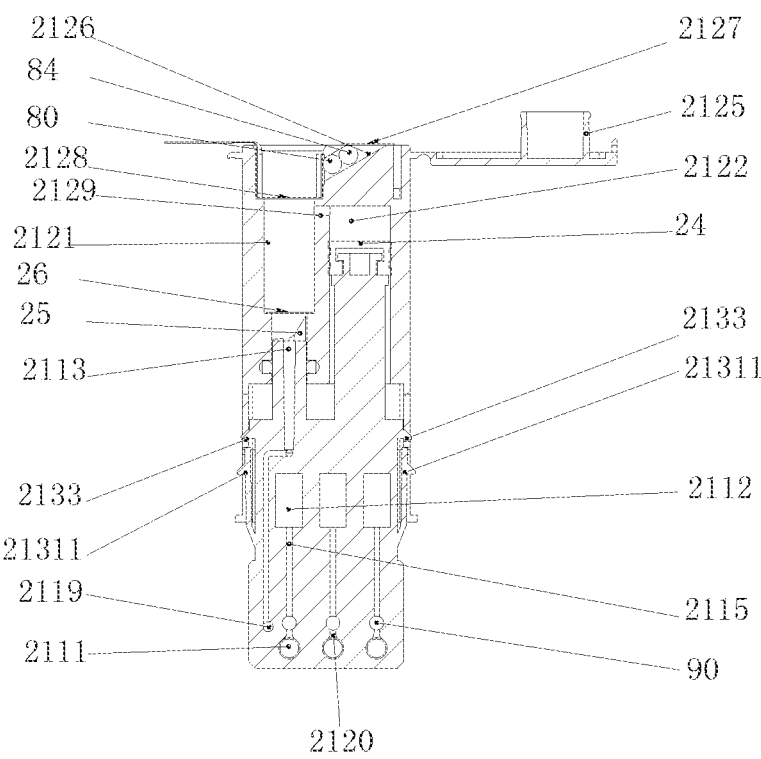
FIG. 2 is a schematic diagram illustrating a cross-section structure of the nucleic acid detection kit provided in Example 1 of the present disclosure (where the kit body does not slide relative to the reagent card)
Figure 3:
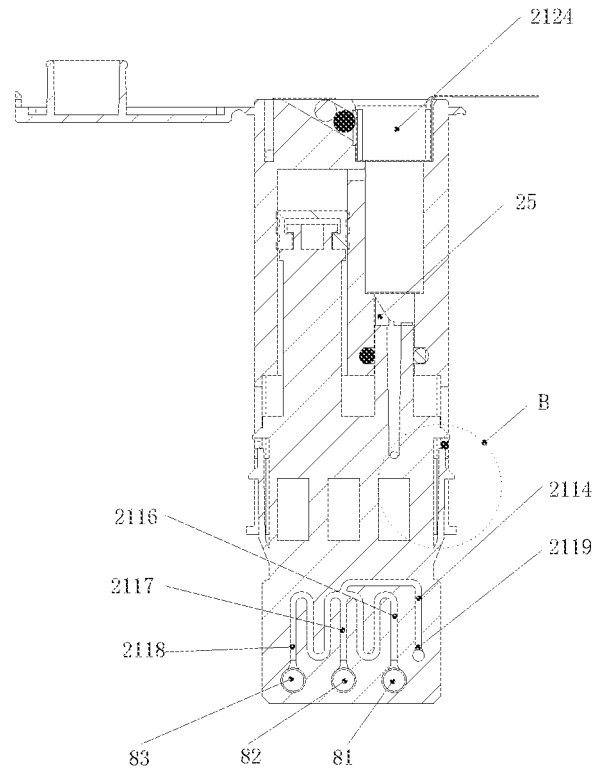
FIG. 3 is a schematic diagram illustrating another cross-section structure of the nucleic acid detection kit provided in Example 1 of the present disclosure (where the kit body does not slide relative to the reagent card)
Figure 4:
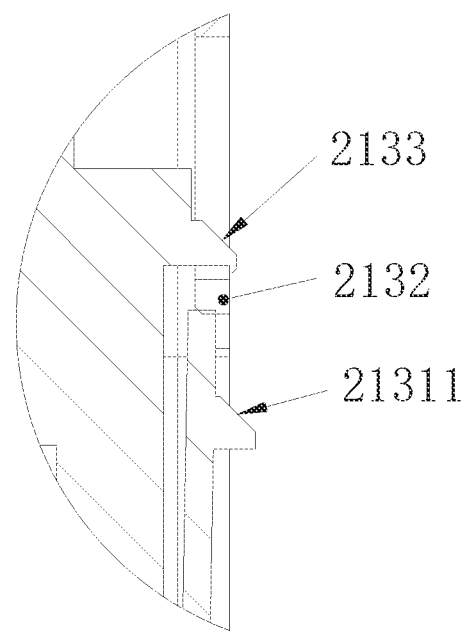
FIG. 4 is a partially enlarged view of zone B in FIG. 3.
Figure 5:
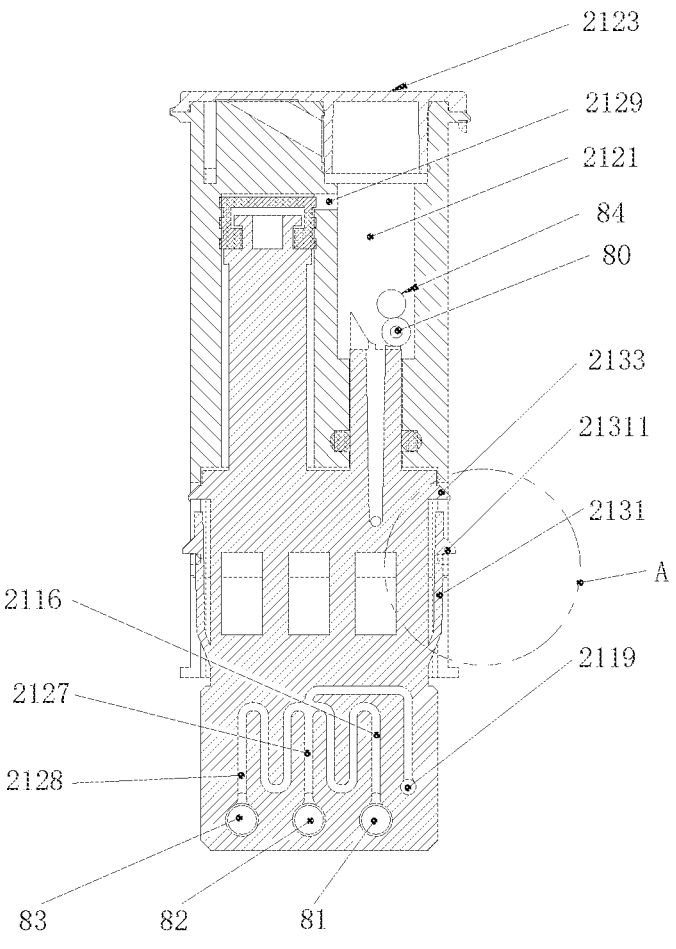
FIG. 5 is a schematic diagram illustrating a cross-section structure of the nucleic acid detection kit provided in Example 1 of the present disclosure (where the kit body slides relative to the reagent card)
Figure 6:
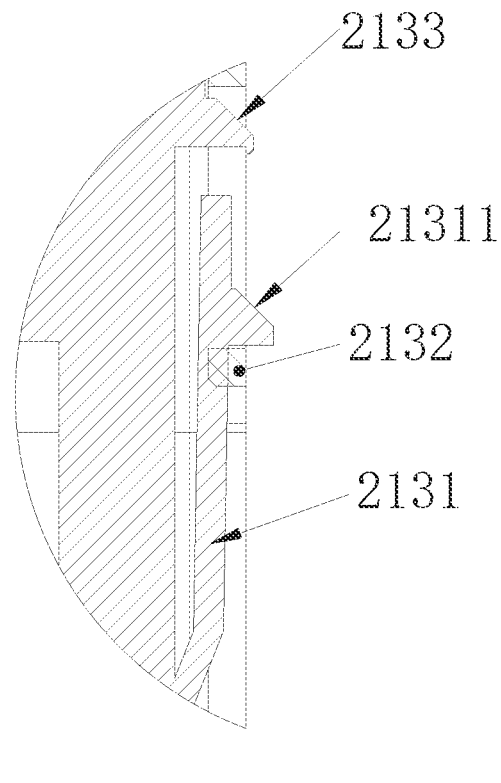
FIG. 6 is a partially enlarged view of zone A in FIG. 5.
Figure 7:
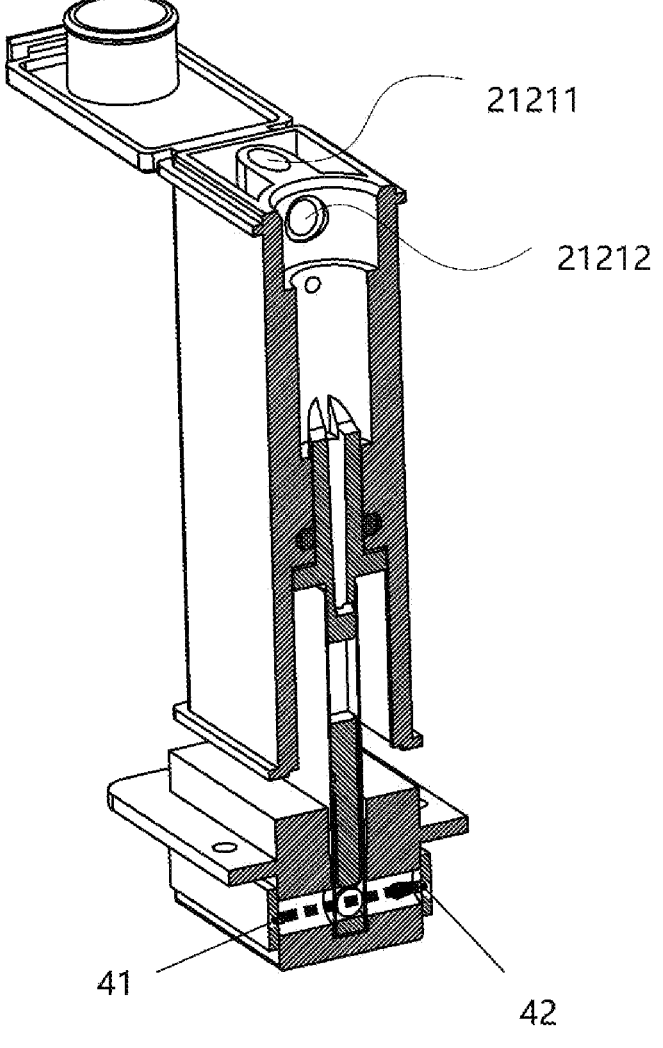
FIG. 7 is a perspective view of the nucleic acid detection kit provided in Example 1 of the present disclosure.
Figure 8:
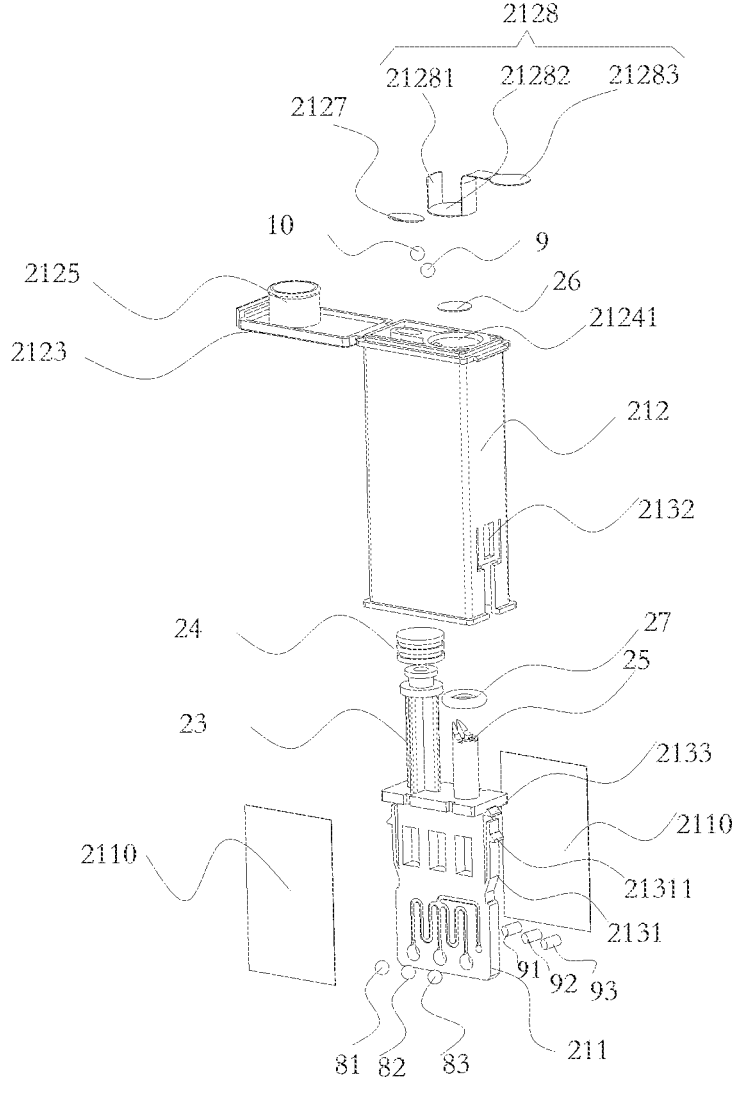
FIG. 8 is a schematic diagram illustrating an exploded structure of the nucleic acid detection kit provided in Example 1 of the present disclosure.

10 represents a first housing; 11 represents a housing body; 12 represents a mounting base plate; 121 represents a circuit board mounting base; 122 represents a back shell mounting bottom notch; 123 represents a circuit board cover plate; 13 represents an upper housing cover; 14 represents a back shell; 15 represents a debugging interface; 16 represents a first power socket; 17 represents a power switch; 18 represents a first light-emitting diode (LED) lamp;

21 represents a nucleic acid detection kit; 22 represents a first circuit board; 23 represents a piston rod; 24 represents a rubber piston; 25 represents a puncture needle; 26 represents a second sealing membrane; 27 represents an O-ring seal;

211 represents a reagent card; 2110 represents a first sealing membrane; 2111 represents a nucleic acid amplification cavity; 2112 represents a gas tail cavity; 2113 represents a sample injection flow channel; 2114 represents a main flow channel; 2115 represents an exhaust gas flow channel; 2116 represents a shunt channel I; 2117 represents a shunt channel II; 2118 represents a shunt channel III; 2119 represents a wax column; 2120 represents a bubble storage cavity;

212 represents a kit body; 2121 represents a liquid cavity; 21211 represents a first lyophilized pellet inlet; 21212 represents a first lyophilized pellet outlet; 2122 represents a gas source cavity; 2123 represents an upper cover; 2124 represents a sample injection port; 2125 represents a protrusion; 2126 represents a QC internal standard cavity; 2127 represents a third sealing membrane; 2128 represents a fourth sealing membrane; 21281 represents a first portion; 21282 represents a second portion; 21283 represents a third portion; 2129 represents a gas source flow channel;

213 represents a buckle assembly; 2131 represents a buckle strip; 21311 represents a first cantilever; 2132 represents a bayonet buckle; 2133 represents a second cantilever;

3 represents a first heating module; 31 represents a heating member; 311 represents a heating groove; 312 represents a first hole; 32 represents a first heating plate;

41 represents a light source; 42 represents a light sensor;

51 represents a front cover; 511 represents a light guide column hole; 512 represents a fixing column; 513 represents a buckle assembly slot; 514 represents a first bottom surface; 515 represents a first side I; 516 represents a second side I; 517 represents a third side I; 52 represents a rear cover; 521 represents a fixing slot; 522 represents a second bottom surface; 523 represents a first side II; 524 represents a second side II; 525 represents a third side II;

6 represents a second heating module; 61 represents a second heating plate; 62 represents a second circuit board; 621 represents a second power socket; 63 represents a temperature sensor; 64 represents a third hole;

71 represents a light guide column; 72 represents a second LED lamp;

80 represents a first lyophilized pellet; 81 represents a lyophilized pellet I; 82 represents a lyophilized pellet II; 83 represents a lyophilized pellet III; 84 represents a plastic ball;

90 represents a check valve; 91 represents a check valve I; 92 represents a check valve II; and 93 represents a check valve III.

DETAILED DESCRIPTION OF THE EMBODIMENTS

The examples of the present disclosure are described below in detail. Implementations of the examples are shown in the accompanying drawings. The same or similar numerals represent the same or similar elements or elements with the same or similar functions throughout the specification. The examples described below with reference to the accompanying drawings are exemplary and are intended to explain the present disclosure but should not be construed as a limitation to the present disclosure.

In the description of the present disclosure, unless otherwise clearly specified, the terms such as "connection", "interconnection", and "fixation" should be understood in a broad sense. For example, the "connection" may be a fixed connection, removable connection, or integral connection; may be a mechanical connection or electrical connection; may be a direct connection or indirect connection through an intermediate medium; and may be a communication or interaction between two elements. A person of ordinary skill in the art may understand specific meanings of the above terms in the present disclosure based on the specific situation.

In the present disclosure, unless otherwise expressly specified and defined, a first feature that is "above" or "below" a second feature may include the first feature being in direct contact with the second feature, or that the first feature and the second feature are not in direct contact with each other but are in contact by another feature therebetween. In addition, the first feature that is "over", "above", and "on" the second feature includes the first feature being directly above and diagonally above the second feature, or simply indicates that a horizontal height of the first feature is above that of the second feature. The first feature that is "beneath", "below", and "under" the second feature includes the first feature being directly below and diagonally below the second feature, or simply indicates that the horizontal height of the first feature is lower than that of the second feature.

The technical solutions of the present disclosure will be described in more detail below with reference to the accompanying drawings and specific implementations.

Example 1

This example of the present disclosure provides a nucleic acid detection kit 21 that can be used completely outside a laboratory. The nucleic acid extraction can be directly completed in the nucleic acid detection kit 21. An internal gas pressure balance system is adopted in the nucleic acid detection kit 21 to store an exhaust gas in the nucleic acid detection kit 21, such that the fully-sealed sample injection and detection can be achieved and the aerosol pollution and other pollution risks are completely eliminated. The sample injection is promoted in the nucleic acid detection kit 21, which reduces the external power of the equipment and simplifies the complexity of the detection equipment.

As shown in FIG. 1 to FIG. 8, a microfluidic nucleic acid detection kit 21 is provided, including a kit body 212 and a reagent card 211 that are interconnected, where the kit body 212 can slide relative to the reagent card 211 to control the kit to work. The microfluidic nucleic acid detection kit further includes a plurality of cavities and a plurality of flow channels that communicate with the plurality of cavities. The plurality of cavities and the plurality of flow channels form a closed system, and the plurality of cavities at least include:

a gas source cavity 2122 arranged in the kit body 212 and capable of controlling a gas pressure of the closed system through a volume change;

a liquid cavity 2121 arranged in the kit body 212 and configured to inject a liquid reagent, where the liquid cavity 2121 communicates with the gas source cavity 2122 through a gas source flow channel 2129;

a nucleic acid amplification cavity 2111 arranged on the reagent card 211, where the nucleic acid amplification cavity 2111 communicates with the liquid cavity 2121 through a sample injection flow channel 2113 and a gas pressure inside the nucleic acid amplification cavity can be 0 kPa to 100 kPa;

a gas tail cavity 2112 arranged on the reagent card 211, where the gas tail cavity 2112 communicates with the nucleic acid amplification cavity 2111 through an exhaust gas flow channel 2115 and a gas pressure inside the gas tail cavity can be 0 kPa to 100 kPa; and a bubble storage cavity 2120 arranged between the exhaust gas flow channel 2115 and the nucleic acid amplification cavity 2111, where the bubble storage cavity 2120 communicates with the nucleic acid amplification cavity 2111, a check valve 90 is provided between the bubble storage cavity 2120 and the exhaust gas flow channel 2115, and the check valve 90 is configured to block the circulation of a liquid and discharge gas.

Specifically, the principle of the plurality of cavities and the plurality of flow channels to form an internal gas pressure balance process in the microfluidic nucleic acid detection kit 21 is as follows: Before the kit body 212 slides relative to the reagent card 211, the gas source cavity 2122 and the gas tail cavity 2112 have the same gas pressure and the liquid in the liquid cavity 2121 will not flow into the nucleic acid amplification cavity 2111.

When the kit body 212 slides relative to the reagent card 211, the gas source cavity 2122 is compressed, the gas pressure in the gas source cavity 2122 increases to push a liquid reagent in the liquid cavity 2121 to be injected through the sample injection flow channel 2113 into the nucleic acid amplification cavity 2111, and the flow of the liquid reagent pushes a gas in the nucleic acid amplification cavity 2111 to be injected into the gas tail cavity 2112.

When the liquid reagent reaches check valve 90, the liquid reagent in the liquid cavity 2121 stops flowing, such that the liquid reagent is accurately injected into the nucleic acid amplification cavity 2111.

Since the whole process of the kit body 212 sliding relative to the reagent card 211 is conducted in the microfluidic nucleic acid detection kit 21, there is no need to form a gas outlet on the detection kit 21, such that the fully-sealed detection can be achieved without pollution.

More specifically, a solid reagent required for nucleic acid amplification is placed in the nucleic acid amplification cavity 2111, and the solid reagent includes a dry powder reagent, a lyophilized pellet for a reagent, or an internal standard reagent for QC. A nucleic acid lysis extract is placed in the liquid cavity 2121 with a space reserved for sample addition, where the liquid cavity 2121 has a volume of 100 μL to 3,000 μL and the nucleic acid lysis extract has a volume of 100 μL to 5,000 μL.

The following formulas are adopted to well explain the principle of the above liquid flow process. As shown in FIG. 2, FIG. 3, FIG. 5, and FIG. 10, the volume of the gas source cavity 2122 is $V_1$, the volume of air in the liquid cavity 2121 is $V_2$, the volume of the nucleic acid amplification cavity 2111 is $V_3$, and the volume of the gas tail cavity 2112 is $V_4$. The pressure P1 of liquid cavity and pressure P2 of gas tail cavity during the liquid flow are as follows:

The cavity pressures at initial lysis buffer flow state:

$$P_1 = \frac{V_1 + V_2}{V_1 + V_2} = 1_{atm} \text{ and } P_2 = \frac{V_3 + V_4}{V_3 + V_4} = 1_{atm};$$

The cavity pressures after the pushing the lysis buffer flow state:

$$P_1 = \frac{V_1 + V_2}{V_2} > 1_{atm} \text{ and } P_2 = \frac{V_3 + V_4}{V_3 + V_4} = 1_{atm};$$

and

The cavity pressures when stopping the lysis buffer flow:

$$P_1 = \frac{V_1 + V_2 - V_3}{V_2}, P_2 = \frac{V_3 + V_4}{V_4}, \text{ and } P_1 > P_2.$$

In the process of the kit body 212 sliding relative to the reagent card 211, when $P_1$ is greater than $P_2$, a lysis buffer flow state changes to a pushed state, and then $P_2$ gradually increases. When the liquid reagent in the liquid cavity 2121 reaches the check valve, the lysis buffer flow state changes to a stopped state, at which point $P_1$ is still greater than $P_2$.

Figure 9:
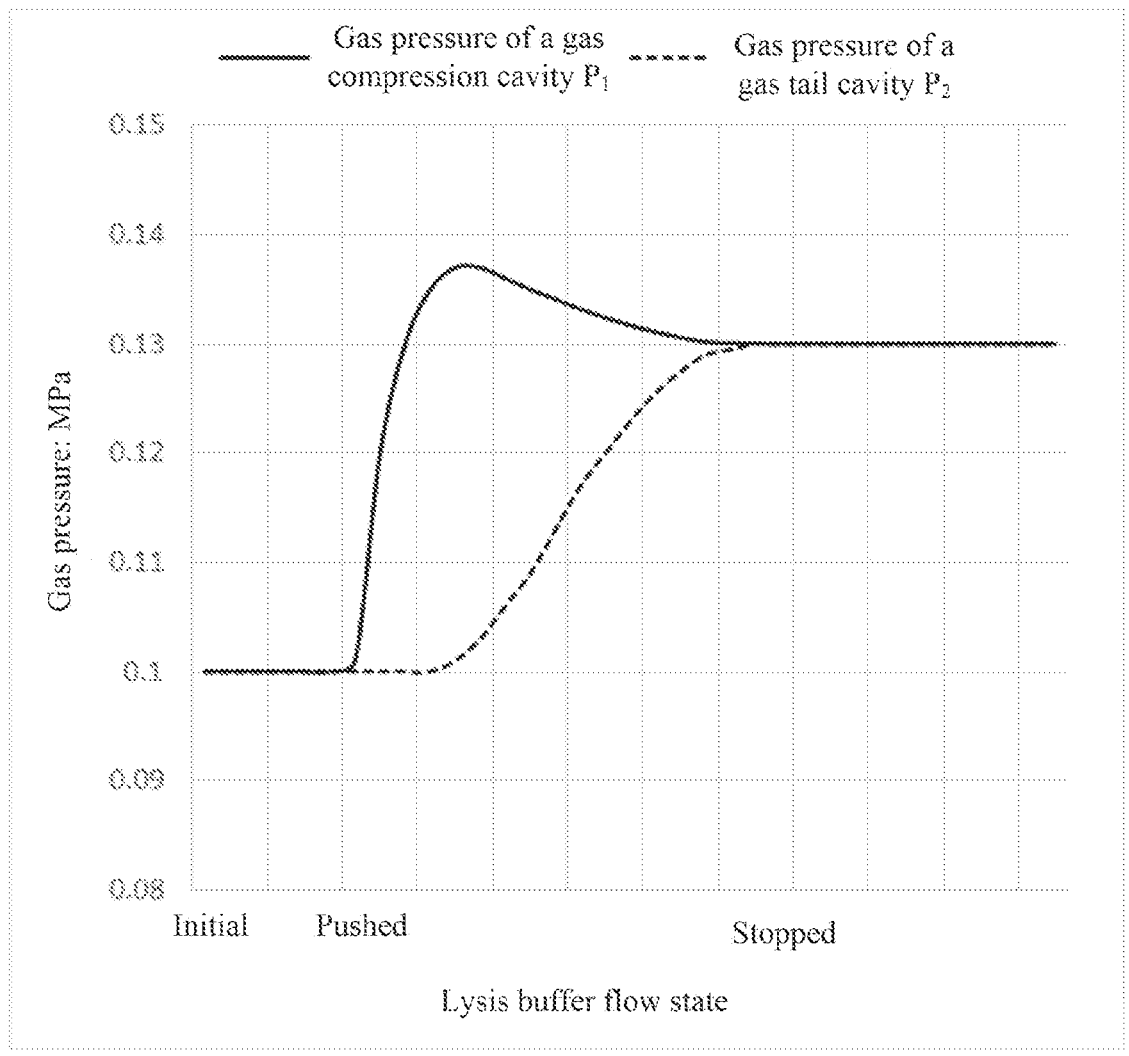
FIG. 9 is a graph representing a gas pressure balance method of the nucleic acid detection kit provided in Example 1 of the present disclosure.
Figure 10:
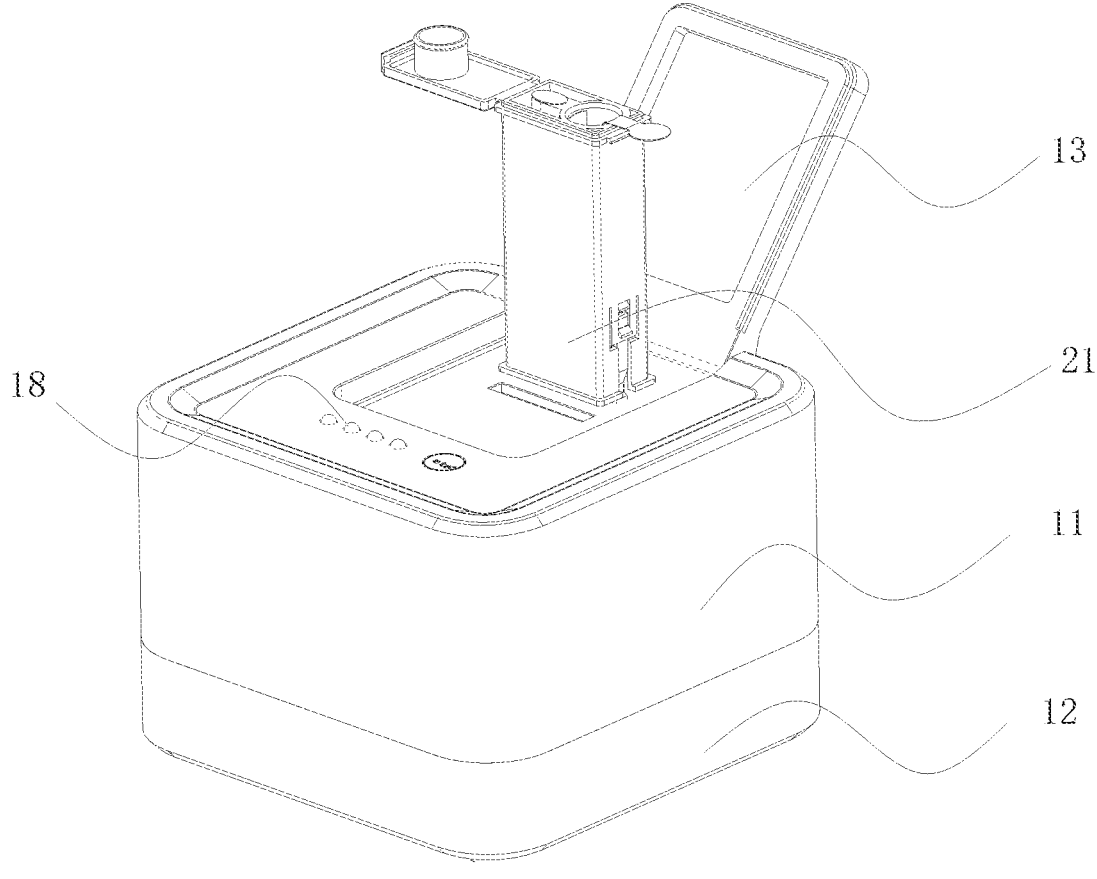
FIG. 10 is a schematic diagram illustrating a three-dimensional (3D) structure of the nucleic acid detection device provided in Example 2 of the present disclosure.
Figure 11:
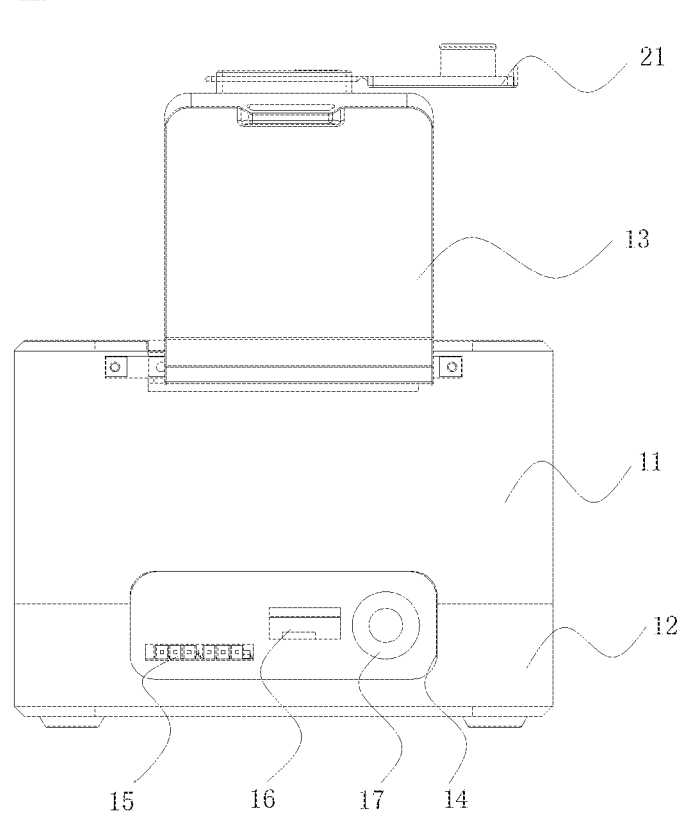
FIG. 11 is a schematic diagram illustrating the rear structure of the nucleic acid detection device provided in Example 2 of the present disclosure.

As shown in FIG. 9, the volume of the gas source cavity 2122 is set as 300 μL, the volume of air in the liquid cavity 2121 is set as 800 μl, the volume of the nucleic acid amplification cavity 2111 is set as 80 μL, and the volume of the gas tail cavity 2112 is set as 500 μL for illustration below:

initial lysis buffer flow state:

$$P_1 = \frac{300 \ \mu l + 800 \ \mu l}{300 \ \mu l + 800 \ \mu l} = 1_{atm} \text{ and } P_2 = \frac{80 \ \mu l + 500 \ \mu l}{80 \ \mu l + 500 \ \mu l} = 1_{atm};$$

starting of a pushed lysis buffer flow state:

$$P_1 = \frac{300 \ \mu l + 800 \ \mu l}{800 \ \mu l} = 1.37_{atm} \text{ and } P_2 = \frac{80 \ \mu l + 500 \ \mu l}{80 \ \mu l + 500 \ \mu l} = 1_{atm};$$

and starting of a stopped lysis buffer flow state:

$$P_1 =$$

$$\frac{300 \ \mu l + 800 \ \mu l - 80 \ \mu l}{800 \ \mu l} = 1.3_{atm} \text{ and } P_2 = \frac{80 \ \mu l + 500 \ \mu l}{500 \ \mu l} = 1.16_{atm}.$$

A main flow channel 2114 is provided between the nucleic acid amplification cavity 2111 and the sample injection flow channel 2113. Specifically, in order to make the liquid cavity 2121 and the nucleic acid amplification cavity 2111 in a closed state during sample lysis, a wax column 2119 is provided between the sample injection flow channel 2113 and the main flow channel 2114, which serves as a valve. When the kit body 212 slides relative to the reagent card 211, the wax column 2119 is in a solid state and the sample injection flow channel 2113 and the main flow channel 2114 are separated by the wax column 2119. The wax column 2119 can be melted by a heating device to make the wax column 2119 change from a solid state to a liquid state, such that the sample injection flow channel 2113 communicates with the main flow channel 2114. The plurality of cavities further includes a QC internal standard cavity 2126 arranged in the kit body 212. A first lyophilized pellet 80 is placed in the QC internal standard cavity 2126, and the first lyophilized pellet 80 includes a reagent component required for internal QC. A second lyophilized pellet or a lyophilized powder is placed in the nucleic acid amplification cavity 2111, and the second lyophilized pellet or the lyophilized powder includes a reagent component required for nucleic acid amplification.

The nucleic acid amplification cavity 2111 and the gas tail cavity 2112 are provided in the same number and correspond to each other, and similarly, a corresponding check valve 90 is provided between a nucleic acid amplification cavity 2111 and a gas tail cavity 2112. Specifically, a number of nucleic acid amplification cavities 2111 can be changed according to actual needs. For ease of description, in this example, the nucleic acid amplification cavity 2111 includes a nucleic acid amplification cavity I, a nucleic acid amplification cavity II, and a nucleic acid amplification cavity III. The gas tail cavity 2112 accordingly includes a gas tail cavity I, a gas tail cavity II, and a gas tail cavity III. The check valve 90 accordingly includes a check valve I 91, a check valve II 92, and a check valve III 93. A bubble storage cavity I is formed between the check valve I 91 and the nucleic acid amplification cavity I. A bubble storage cavity II is formed between the check valve II 92 and the nucleic acid amplification cavity II, and a bubble storage cavity III is formed between the check valve III 93 and the nucleic acid amplification cavity III. The gas tail cavity 2112 communicates with the nucleic acid amplification cavity 2111 through the exhaust gas flow channel 2115, that is, the check valve 90 is arranged on the exhaust gas flow channel 2115. Thus, the nucleic acid amplification cavity I communicates with the main flow channel 2114 through a shunt channel I 2116, the nucleic acid amplification cavity II communicates with the main flow channel 2114 through a shunt channel II 2117, and the nucleic acid amplification cavity III communicates with the main flow channel 2114 through a shunt channel III 2118. A lyophilized pellet I 81 is pre-filled in the nucleic acid amplification cavity I. A lyophilized pellet II 82 is pre-filled in the nucleic acid amplification cavity II. A lyophilized pellet III 83 is pre-filled in the nucleic acid amplification cavity III 2111. The lyophilized pellet I 81, the lyophilized pellet II 82, and the lyophilized pellet III 83 are reagent systems (enzyme, template concentration, and primer) required for amplification. Primers for the lyophilized pellet I 81, the lyophilized pellet II 82, and the lyophilized pellet III 83 are different, and are a target point I primer for a target sample, a target point II primer for a target sample, and a primer for an internal standard, respectively. The internal gas pressure of each of the lyophilized pellet I 81, the lyophilized pellet II 82, and the lyophilized pellet III 83 can be 0 kPa to 100 kPa.

The end of the sample injection flow channel 2113 close to the liquid cavity 2121 is provided with a puncture needle 25. The combination of the sample injection flow channel 2113 and the puncture needle 25 is a puncture tube, and an O-ring seal 27 is provided between the puncture tube and an extraction cavity. The puncture needle 25 can be inserted into the liquid cavity 2121 to make the puncture needle 25 extend into the liquid cavity 2121, such that the sample injection flow channel 2113 communicates with the liquid cavity 2121. The sample injection flow channel 2113 tapers from the end away from the main flow channel 2114 to the end close to the main flow channel 2114. The reagent card 211 is provided with a piston rod 23, and the end of the piston rod 23 is provided with a rubber piston 24.

The gas source cavity 2122 is shaped like a blind hole on the kit body 212. The end of the piston rod 23 provided with a rubber piston 24 extends into a blind end of the gas source cavity 2122 through an open end of the gas source cavity 2122. The gas source flow channel 2129 is arranged near the blind end of the gas source cavity 2122. Before the kit body 212 slides relative to the reagent card 211, the rubber piston 24 is located in the gas source cavity 2122 at a position lower than the gas source flow channel 2129. In this example, the distance between the rubber piston 24 and the blind end is 1 mm to 10 mm and preferably 5 mm. When the kit body 212 slides relative to the reagent card 211, the rubber piston 24 moves toward the blind end to feed gas from the gas source cavity into the liquid cavity 2121.

Specifically, a sample injection port 2124 is formed on the kit body 212, and the sample injection port 2124 can communicate with the liquid cavity 2121. The nucleic acid detection kit 21 further includes an upper cover 2123 connected with the kit body 212, and the upper cover 2123 is provided with a protrusion 2125 to seal the sample injection port 2124. A first lyophilized pellet inlet 21211 and a first lyophilized pellet outlet 21212 are formed in the QC internal standard cavity 2126, and the first lyophilized pellet outlet 21212 communicates with the liquid cavity 2121 and the QC internal standard cavity 2126. The upper cover 2123 can also cover the first lyophilized pellet inlet 21211.

Specifically, the first lyophilized pellet 80 is an internal standard for verification of a lysis buffer stored in the liquid cavity 2121, a lysis buffer stored in the nucleic acid amplification cavity 2111, a lyophilized pellet system stored in the nucleic acid amplification cavity 2111, a heating module, a detection module, and a display module. The bottom of the QC internal standard cavity 2126 is inclined at a specified angle with a horizontal plane, and the first lyophilized pellet outlet 21212 is located at the lowest position of the inclined bottom, such that the first lyophilized pellet 80 can move downward along the inclined bottom and enter the liquid cavity 2121 through the first lyophilized pellet outlet 21212. In this example, considering the light weight of the first lyophilized pellet 80, a plastic ball 84 is pre-stored in the QC internal standard cavity 2126, and the plastic ball 84 can be a polypropylene (PP) plastic ball. During a detection process, the plastic ball 84 can push the first lyophilized pellet 80 smoothly into the liquid cavity 2121 under the action of its own gravity and the inclined bottom.

Specifically, the end of the liquid cavity 2121 away from the sample injection port 2124 is provided with a second sealing membrane 26, and the puncture needle 25 can be inserted into the liquid cavity 2121 to make the end of the puncture needle 25 penetrate through the second sealing membrane 26 to communicate with the liquid cavity 2121. The third sealing membrane 2127 is arranged at the first lyophilized pellet inlet 21211, a fourth sealing membrane 2128 is arranged at the first lyophilized pellet outlet 21212, and the second sealing membrane 26 and the third sealing membrane 2127 can be each an aluminum membrane. The wax column 2119, the sample injection flow channel 2113, the main flow channel 2114, the exhaust gas flow channel 2115, the nucleic acid amplification cavity 2111, and the gas tail cavity 2112 are sealed by a first sealing membrane 2110, and the first sealing membrane 2110 can be an aluminum membrane.

More specifically, the fourth sealing membrane 2128 includes a first portion 21281, a second portion 21282, and a third portion 21283 that are integrally formed. The first portion 21281, the second portion 21282, and the third portion 21283 have similar "concave" shapes. The first portion 21281 seals the first lyophilized pellet outlet 21212, the second portion 21282 seals an upper end of the liquid cavity 2121, and the third portion 21283 is a ring-pull structure and can extend out of the sample injection port 2124. When a sample needs to be injected, only the third portion 21283 needs to be pulled by hand to take out the fourth sealing membrane 2128. In this example, the fourth sealing membrane 2128 can be an aluminum-plastic composite membrane.

It can be seen from FIG. 1 to FIG. 8 that the nucleic acid detection kit 21 includes a kit body 212 and a reagent card 211 that are connected through a connector.

Specifically, the connector to connect the kit body 212 and the reagent card 211 is a buckle assembly 213 including a buckle fastener arranged on the reagent card 211 and a bayonet buckle 2132 arranged on the kit body 212. The buckle fastener includes a buckle strip 2131. One end of the buckle strip 2131 is connected with the reagent card 211, and the other end of the buckle strip is a free end that extends toward the kit body 212 along the buckle strip 2131. The buckle strip 2131 is provided with a first cantilever 21311, the reagent card 211 is provided with a second cantilever 2133, and the second cantilever 2133 is located above the first cantilever 21311. The bayonet buckle 2132 includes a first bayonet corresponding to the first cantilever 21311 and a second bayonet corresponding to the second cantilever 2133.

When the puncture needle 25 does not extend into the liquid cavity 2121, that is, when the kit body 212 does not slide downward relative to the reagent card 211, the first cantilever 21311 and the second cantilever 2133 both abut against the kit body 212 to ensure that there will be no displacement between the reagent card 211 and the kit body 212.

When the puncture needle 25 extends into the liquid cavity 2121, that is, after the sliding of the kit body 212 relative to the reagent card 211 is completed, the first cantilever 21311 is coupled with the first bayonet and the second cantilever 2133 is coupled with the second bayonet.

The microfluidic nucleic acid detection kit 21 can be used completely outside the laboratory. The nucleic acid extraction can be directly completed in the nucleic acid detection kit 21. An internal gas pressure balance system is adopted in the nucleic acid detection kit 21 to store an exhaust gas in the nucleic acid detection kit 21, such that the fully-sealed sample injection and detection can be achieved and the aerosol pollution and other pollution risks are completely eliminated. The sample injection is promoted in the nucleic acid detection kit 21, which reduces the external power of the equipment.

Example 2

As shown in FIG. 10 to FIG. 14, a nucleic acid detection device is provided, including a first housing 10 (the first housing 10 has a housing body 11 and the microfluidic nucleic acid detection kit 21 provided in Example 1 is arranged in the housing body 11), a first heating module, and a first detection module. The nucleic acid detection device also includes a display module arranged on the housing body 11. The display module includes an LED lamp with a display function, which is convenient for an operator to determine a detection result. In order to facilitate the support, a mounting base plate 12 is provided at the bottom of the housing body 11, and the housing body 11 is connected with the mounting base plate 12.

The housing body 11 has an opening formed at an upper end face and an upper housing cover 13 that is rotatably connected with the housing body 11 and configured to cover the opening. The nucleic acid detection kit 21 is inserted into the opening. The housing body 11 is provided with a mounting position for arranging the display module, and the display module is arranged at the mounting position.

The back side of the housing body 11 is provided with a back shell 14. The mounting base plate 12 is provided with a back shell 14 mounting bottom notch 122. The housing body 11 is provided with a back shell 14 mounting upper notch. The back shell 14 is clamped between the bottom notch 122 and the upper notch. The back shell 14 is provided with a debugging interface 15, a first power socket 16, and a power switch 17 interface. In order to realize automatic control, a power module, a data transmission and processing module, and a control module are also provided in the housing body 11. The nucleic acid detection device also has Bluetooth and WIFI functions, which can be operated remotely by a mobile terminal. The status, data, and detection result of the nucleic acid detection device can be viewed in real-time by a mobile terminal. A principle of electrical control is not repeated here and can refer to the prior art.

Figure 13:
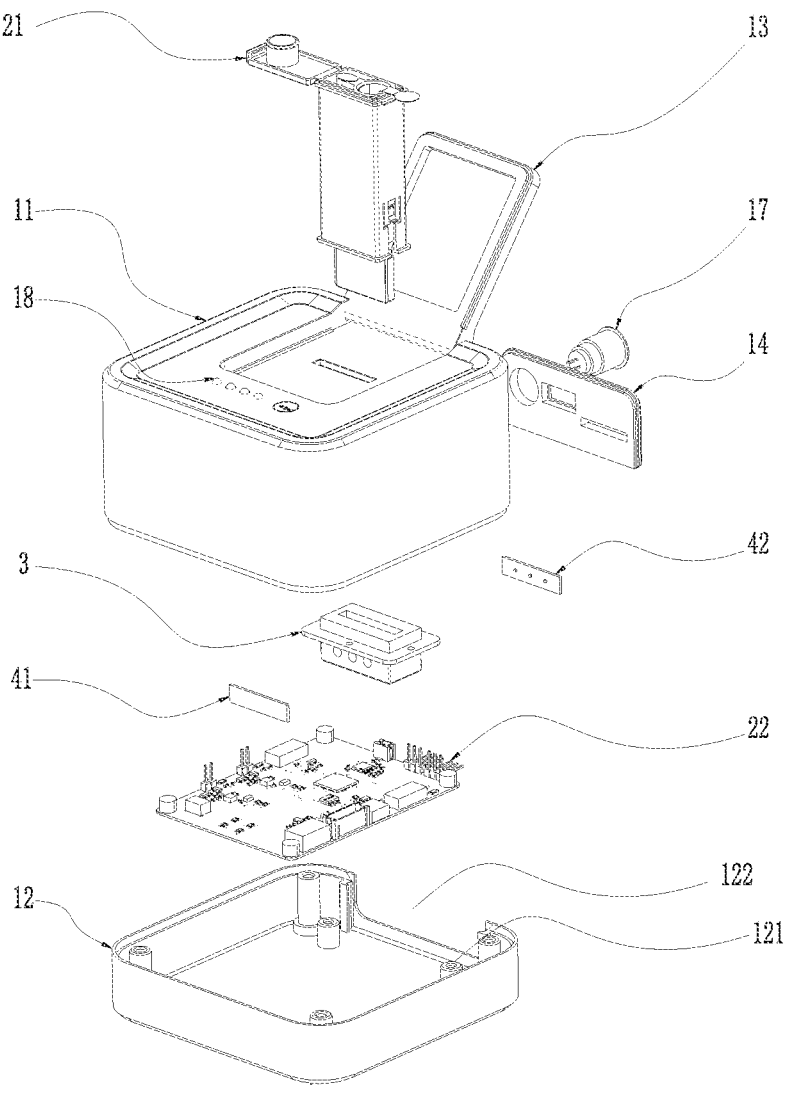
FIG. 13 is a schematic diagram illustrating an exploded structure of the nucleic acid detection device provided in Example 2 of the present disclosure.

As shown in FIG. 13, the nucleic acid detection device includes a first circuit board 22 arranged on the mounting base plate 12 in the first housing 10 and a control unit arranged on the first circuit board 22. The nucleic acid detection kit 21 can be inserted into the opening on the housing body 11. The control unit is electrically connected with the first heating module 3 to control the first heating module 3 to heat the nucleic acid amplification cavity 2111.

Figure 12:
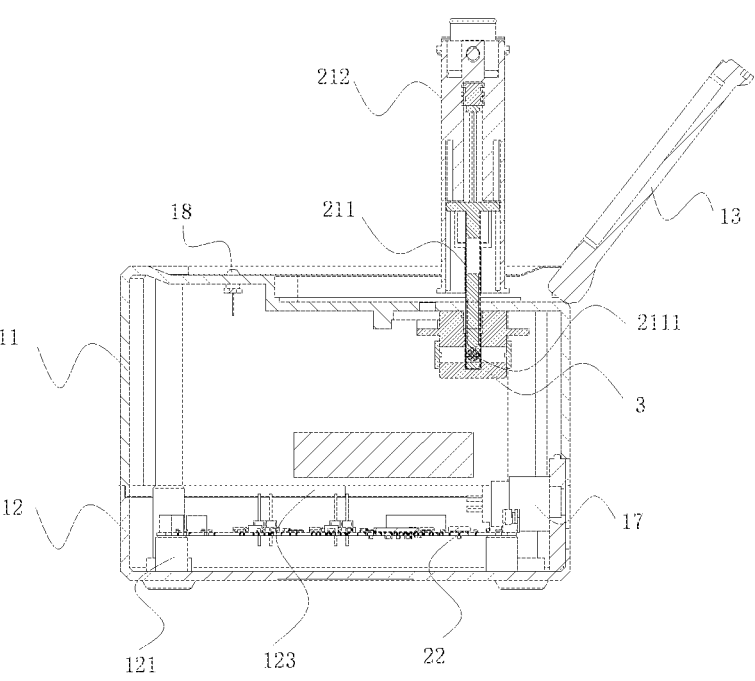
FIG. 12 is a schematic diagram illustrating a cross-section structure of the nucleic acid detection device provided in Example 2 of the present disclosure.
Figure 14:
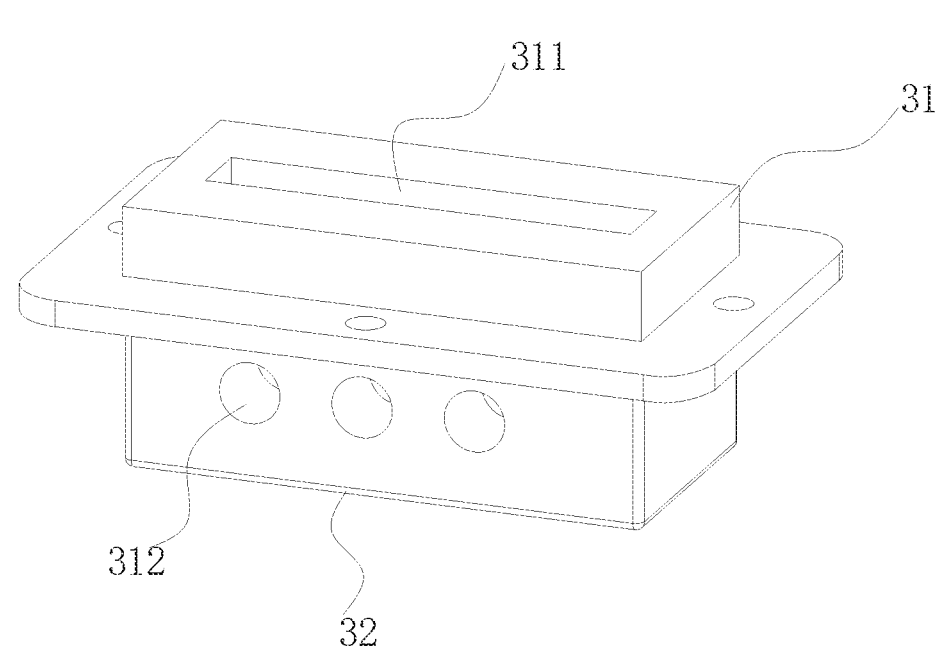
FIG. 14 is a schematic diagram illustrating the structure of the heating member provided in Example 2 of the present disclosure.
Figure 15:
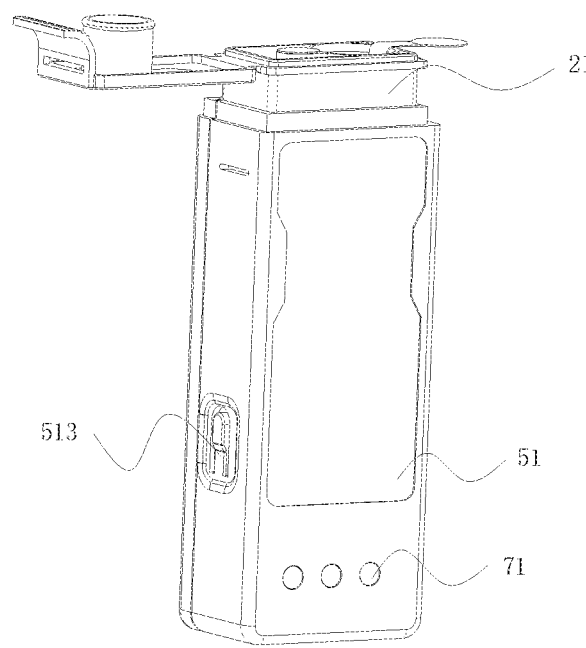
FIG. 15 is a schematic diagram illustrating a 3D structure of the integrated detection device provided in Example 3 of the present disclosure.
Figure 16:
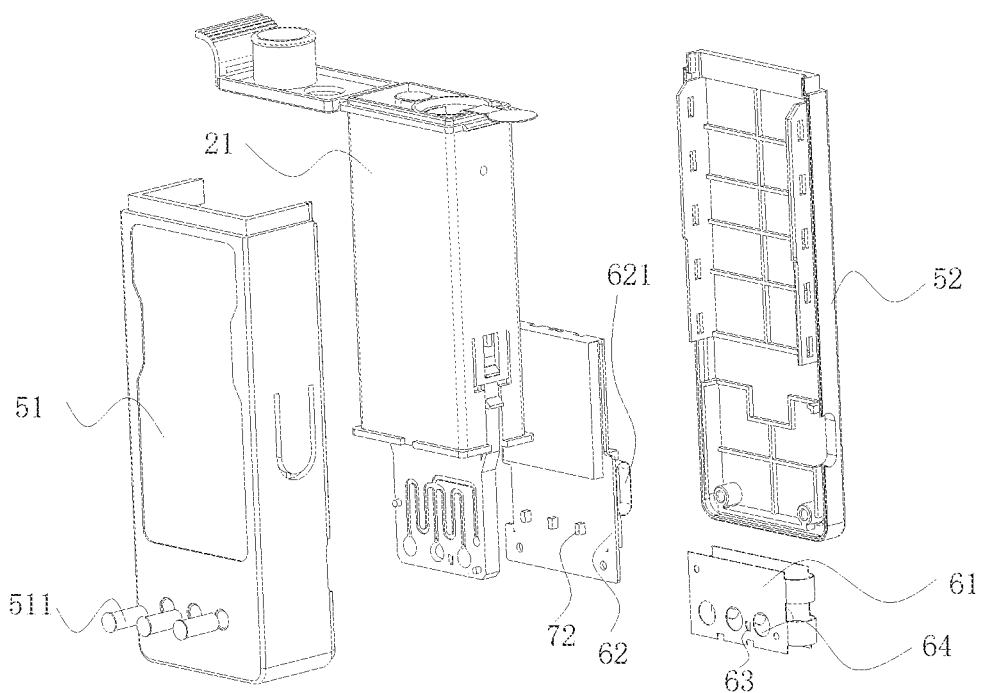
FIG. 16 is an exploded view of the integrated detection device provided in Example 3 of the present disclosure.

As shown in FIG. 12, FIG. 13, and FIG. 14, the first heating module 3 includes a heating member 31 closely surrounding a reaction cavity, a first heating plate 32 that is arranged at a bottom of the heating member 31 and is in contact with the heating member 31 for heat conduction, and a temperature sensor adjacent to the first heating plate 32. The temperature sensor is electrically connected to the control unit, and a heat dissipation space is formed between the first heating module 3 and the first circuit board 22.

Specifically, the heating member 31 is provided with a heating groove 311 matching the nucleic acid amplification cavity 2111 arranged in the reagent card 211. The nucleic acid amplification cavity 2111 can extend into the heating groove 311. A first hole 312 and a second hole are formed oppositely in the heating member 31. The first hole 312 and the second hole both penetrate through the heating groove 311. The nucleic acid amplification cavity 2111 is arranged between the first hole 312 and the second hole.

In this example, the first hole 312 includes a first hole I, a first hole II, and a first hole III. The second hole also includes a second hole I corresponding to the first hole I, a second hole II corresponding to the first hole II, and a second hole III corresponding to the first hole III. The nucleic acid amplification cavity I is arranged between the first hole I and the second hole I. The nucleic acid amplification cavity II is arranged between the first hole II and the second hole II, and the nucleic acid amplification cavity III is arranged between the first hole III and the second hole III.

The first detection module can design different detection methods according to needs, and the nucleic acid detection methods include fluorescence hybridization, loop-mediated isothermal amplification (LAMP), real-time fluorescent polymerase chain reaction (PCR), high-resolution melting analysis (HRM), electrochemical aptamer-based analysis, or the like. A corresponding detection module is designed according to a detection method.

In this example, the first detection module includes a light source 41 and a light sensor 42 that are electrically connected with the first circuit board 22. The light source 41 and the light sensor 42 both are arranged outside the heating member 31. The light source 41 is attached to the first hole 312, and the light sensor 42 is attached to the second hole. Specifically, the first heating module 3 heats the nucleic acid amplification cavity I, the nucleic acid amplification cavity II, and the nucleic acid amplification cavity III. The light source 41 reaches the light sensor 42 through the nucleic acid amplification cavity I, the nucleic acid amplification cavity II, and the nucleic acid amplification cavity III. The light sensor 42 receives a change value of an optical signal.

In this example, the first circuit board 22 is arranged on the circuit board mounting base 121. The circuit board mounting base 121 is arranged in the mounting base plate 12. The first circuit board 22 is provided with a circuit board cover plate 123. The first circuit board 22 includes a processing unit configured to process and analyze an optical signal acquired by the first detection module 3 and then feed an analysis result back to the display module.

Specifically, the processing unit includes a data acquisition circuit, an ADC chip, and a processor. A signal from the light sensor is acquired by the data acquisition circuit, subjected to analog-to-digital conversion by the ADC chip, and transmitted to the processor for processing and analysis of a digital signal, and an analysis result is fed back to the display module. That is, the processing unit first acquires an optical signal on the light sensor, then the optical signal is fed back to an LED lamp, a changed optical signal is subjected to analog-to-digital conversion and then transmitted to the processor for processing and analysis of a digital signal, and an analysis result is fed back to the display module.

The specific operation steps were as follows:

1. Sample Injection

An upper cover 2123 of the kit body 212 is opened and the aluminum composite membrane is removed, such that the first lyophilized pellet 80 falls into the liquid cavity 2121 under a pushing action of the plastic ball 84. A throat swab is rinsed more than ten times in a lysis buffer, and during the process of repeatedly rinsing the throat swab, the first lyophilized pellet 80 is evenly dispersed in the lysis buffer. After the rinsing is completed, the kit body is covered by the upper cover 2123.

2. Lysis

The reagent card 211 of the nucleic acid detection kit 21 is inserted into the opening on the housing body 11, and the kit body 212 is gently pressed down until the first cantilever is coupled with the first bayonet and the second cantilever is coupled with the second bayonet, such that the puncture needle 25 punctures the second sealing membrane 26 and the rubber piston 24 pushes gas from the gas source cavity 2122 to the liquid cavity 2121, thereby increasing gas pressure in the liquid cavity 2121. In this example, considering the consistency of a liquid entering the nucleic acid amplification cavity 2111, atmospheric pressure in the liquid cavity 2121 is 0.137 MPa and a sample is lysed in the lysis buffer for 10 min.

3. Amplification

After a sample is lysed in a lysis buffer for 10 min, the first heating module 3 heats the wax column 2119 to melt the wax column 2119, such that all flow channels are open. Under the action of a pressure difference, a liquid enters the main flow channel 2114 through the sample injection flow channel 2113 and then enters the nucleic acid amplification cavity I, the nucleic acid amplification cavity II, and the nucleic acid amplification cavity III through shunt channels. A lyophilized pellet I 81 is pre-embedded in the nucleic acid amplification cavity I, a lyophilized pellet II 82 is preembedded in the nucleic acid amplification cavity II 2111, and a lyophilized pellet III 83 is pre-embedded in the nucleic acid amplification cavity III. During the above process, the first heating module 3 heats the nucleic acid amplification cavity I, the nucleic acid amplification cavity II, and the nucleic acid amplification cavity III.

4. Detection

After the amplification is completed, amplification results of the nucleic acid amplification cavity I, the nucleic acid amplification cavity II, and the nucleic acid amplification cavity III are detected.

The device involves simple and convenient operations. The sample extraction can be conducted at the sample injection port, and there is no gas outlet in the nucleic acid detection kit 21, such that the nucleic acid detection kit can achieve fully-sealed detection without pollution and can be used completely outside the laboratory. The nucleic acid detection device can achieve the sample injection under the pushing action in the card without external power, and the nucleic acid detection device is simple, which simplifies the complexity of the detection equipment.

Example 3

As shown in FIG. 15 to FIG. 19, this example provides an integrated nucleic acid detection device, including the microfluidic nucleic acid detection kit 21 provided in Example 1 and a second housing configured to accommodate the nucleic acid detection kit 21. The second housing can be integrated, or the second housing can also include a front cover 51 and a rear cover 52 for holding the nucleic acid detection kit 21, and the nucleic acid detection kit 21 is arranged between the front cover 51 and the rear cover 52. The integrated detection device further includes a second heating module 6 configured to heat the nucleic acid amplification cavity 2111 and a second detection module arranged between the front cover 51 and the rear cover 52 and configured to detect a change of an optical signal in the nucleic acid amplification cavity 2111. The optical signal includes one or more selected from the group consisting of color, brightness, and fluorescence saturation signals.

The nucleic acid detection kit 21 and the detection device in the integrated nucleic acid detection device are integrated to produce an integrated nucleic acid detection device, and the nucleic acid detection kit is disposable and can be changed after one-time detection, which prevents the detection device from contaminating the reagent card. In addition, the integrated nucleic acid detection device can be used completely outside a laboratory, which can achieve fullysealed sample injection and detection and completely eliminate aerosol pollution and other pollution risks.

Figure 17:
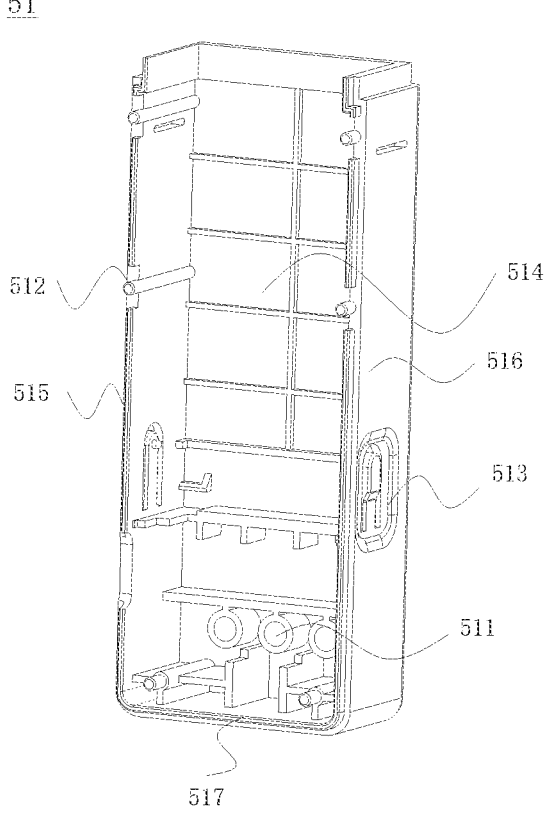
FIG. 17 is a schematic diagram illustrating a 3D structure of the front cover of the integrated detection device provided in Example 3 of the present disclosure.
Figure 18:
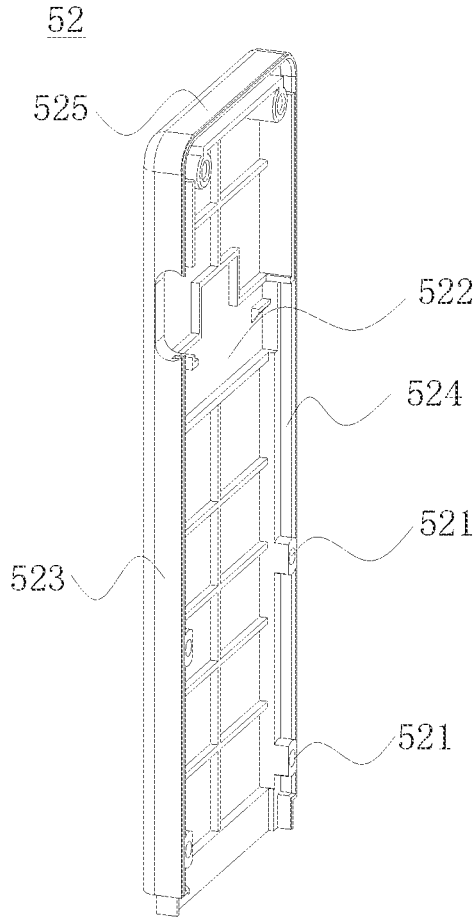
FIG. 18 is a schematic diagram illustrating a 3D structure of a rear cover of the integrated detection device provided in Example 3 of the present disclosure.

Specifically, as shown in FIG. 17 and FIG. 18, the front cover 51 and the rear cover 52 can be in a clamped connection. The front cover 51 includes a first bottom surface 514, a first side I 515, a second side I 516, and a third side I 517 that are integrally formed. The first bottom surface 514, the first side I 515, the second side I 516, and the third side I 517 enclose a "concave" shape. The first side I 515 and the second side I 516 are symmetrically arranged at two sides of the first bottom surface 514, and a plurality of fixing columns 512 are symmetrically arranged on the first side I

515 and the second side I 516 to connect the rear cover 52. The rear cover 52 has a "concave" shape and includes a second bottom surface 522, a first side II 523, a second side II 524, and a third side II 525 that are integrally formed. The first side II 523 and the second side II 524 are symmetrically arranged at two sides of the second bottom surface 522. Fixing slots 521 matching the fixing columns 512 are symmetrically arranged on the first side II 523 and the second side II 524. The front cover 51 and rear cover 52 are clamped together by clamping the fixing columns 512 with the fixing slots 521. The first side I 515 is docked with the first side II 523 to form a first side edge of the housing, the second side I 516 is docked with the second side II 524 to form a second side edge of the housing, and the third side I 517 is docked with the third side II 525 to form the bottom plate of the housing. A cavity formed after the front cover 51 is docked with the rear cover 52 can accommodate the microfluidic nucleic acid detection kit 21 in the above example, and a cavity enclosed by the front cover 51 and the rear cover 52 of the kit body 212 of the nucleic acid detection kit 21 is exposed.

A second circuit board 62 is also provided between the front cover 51 and the rear cover 52. The end of the second circuit board 62 is inserted into the kit body 212 of the nucleic acid detection kit 21, and the other end is exposed outside the kit body 212 and is flush with the reagent card 211. The second circuit board 62 is provided with a second LED lamp 72 and a control unit. The control unit is electrically connected with the second heating module 6 to control the second heating module 6 to heat the nucleic acid amplification cavity 2111. The second circuit board 62 is also provided with a second power socket 621, and a gap is reserved at the side edge of each of the front cover 51 and the rear cover 52 to expose the second power socket 621. The second circuit board 62 is provided with a data communication unit configured to transmit the detection data to a wireless terminal. The wireless terminal includes, but is not limited to, a mobile terminal, a computer, or a network server. In this example, the second circuit board 62 is arranged on the rear cover 52, and the second circuit board 62 includes a processing unit configured to process and analyze an optical signal acquired by the detection module to obtain detection data.

Specifically, the processing unit includes a data acquisition circuit, an ADC chip, and a processor. A signal from the temperature sensor 63 is acquired by the data acquisition circuit and subjected to analog-to-digital conversion by the ADC chip, and an analysis result is fed back to the processing unit.

Figure 19:
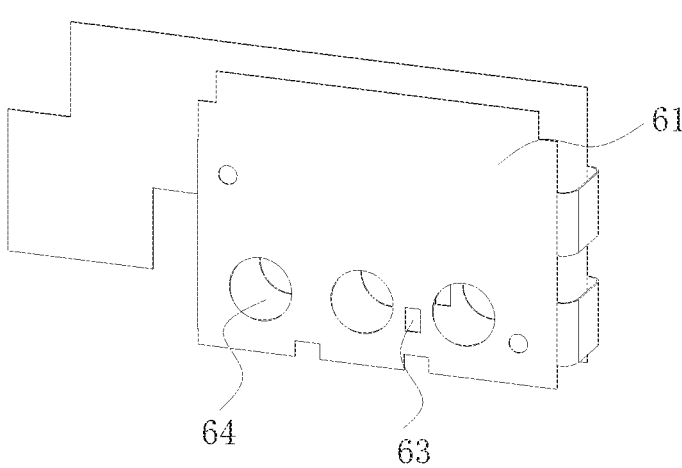
FIG. 19 is a schematic diagram illustrating a structure of a heating module of the integrated detection device provided in Example 3 of the present disclosure.

As shown in FIG. 19, the second heating module 6 includes a second heating plate 61. Two second heating plates 61 are oppositely arranged. One end of one of the two second heating plates 61 is connected with one end of the other one of the two second heating plates through a connector, and the other end of each of the two second heating plates 61 is opened. The two second heating plates 61 enclose the nucleic acid amplification cavity 2111. Three third holes 64 are formed on one of the two second heating plates 61, and fourth holes corresponding to the third holes 64 are formed on the other one of the two second heating plates. Three third holes and three fourth holes are provided to surround the nucleic acid amplification cavity I, the nucleic acid amplification cavity II, and the nucleic acid amplification cavity III, respectively.

The second detection module can design different detection methods according to needs, and the nucleic acid detection methods include fluorescence hybridization, LAMP, real-time fluorescent PCR, HRM analysis, electrochemical aptamer-based analysis, or the like. A corresponding detection module is designed according to a detection method.

In this example, the second detection module includes a second LED lamp 72 (a light source) and a light guide column 71 that are electrically connected to the second circuit board 62. The LED lamp 72 and the light guide column 71 are respectively arranged at two sides of the reagent card 211. Specifically, the second heating module 6 heats the nucleic acid amplification cavity I, the nucleic acid amplification cavity II, and the nucleic acid amplification cavity III. The LED lamp 72 reaches the light guide column 71 through the nucleic acid amplification cavity I, the nucleic acid amplification cavity II, and the nucleic acid amplification cavity III. A user can observe a color change in the light guide column 71.

The above implementations only illustrate the basic principle and characteristics of the present disclosure, and the present disclosure is not limited to the above implementations. Various variations and alterations can be made to the present disclosure without departing from the spirit and scope of the present disclosure, and such variations and alterations shall fall within the protection scope of the present disclosure. The claimed protection scope of the present disclosure is defined by the appended claims and equivalents thereof.

What is claimed is:

1. A microfluidic nucleic acid detection kit, comprising a kit body and a reagent card, wherein the kit body and the reagent card are interconnected, the kit body is configured to slide relative to the reagent card to control the microfluidic nucleic acid detection kit to work; the microfluidic nucleic acid detection kit further comprises a plurality of cavities and a plurality of flow channels, the plurality of flow channels communicates with the plurality of cavities; the plurality of cavities and the plurality of flow channels form a closed system; and the plurality of cavities at least comprises:

a gas source cavity arranged in the kit body and configured for controlling a gas pressure of the closed system through a volume change;

a liquid cavity arranged in the kit body and configured to inject a liquid reagent, wherein the liquid cavity communicates with the gas source cavity through a gas source flow channel;

a nucleic acid amplification cavity arranged on the reagent card, wherein the nucleic acid amplification cavity communicates with the liquid cavity through a sample injection flow channel;

a gas tail cavity arranged on the reagent card, wherein the gas tail cavity communicates with the nucleic acid amplification cavity through an exhaust gas flow channel; and a first sealing membrane arranged on the reagent card, wherein the first sealing membrane seals the sample injection flow channel, the exhaust gas flow channel, and the gas tail cavity.

2. The microfluidic nucleic acid detection kit according to claim 1, wherein a check valve is provided at the exhaust gas flow channel, and the check valve is configured to block the-a circulation of a liquid and discharge a gas.

3. The microfluidic nucleic acid detection kit according to claim 1, wherein the plurality of cavities further comprises a bubble storage cavity, the bubble storage cavity is arranged between the exhaust gas flow channel and the nucleic acid amplification cavity, and the bubble storage cavity communicates with the nucleic acid amplification cavity.

4. The microfluidic nucleic acid detection kit according to claim 1, wherein the kit body and the reagent card are connected through a buckle assembly; the buckle assembly comprises a buckle fastener arranged on the reagent card and a bayonet buckle arranged on the kit body;

the buckle fastener comprises a buckle strip; a first end of the buckle strip is connected with the reagent card, and a second end of the buckle strip is a free end extending toward the kit body along the buckle strip; the buckle strip is provided with a first cantilever and the reagent card is provided with a second cantilever; the second cantilever is located above the first cantilever; and the bayonet buckle comprises a first bayonet corresponding to the first cantilever and a second bayonet corresponding to the second cantilever.

5. The microfluidic nucleic acid detection kit according to claim 4, wherein before the kit body slides relative to the reagent card, both the first cantilever and the second cantilever abut against the kit body, the gas source cavity and the gas tail cavity have a same gas pressure, and a liquid in the liquid cavity does not flow into the nucleic acid amplification cavity; and when the kit body slides relative to the reagent card, the gas source cavity is squeezed, a gas pressure in the gas source cavity increases to push a liquid reagent in the liquid cavity to be injected through the sample injection flow channel into the nucleic acid amplification cavity, a flow of the liquid reagent pushes a gas in the nucleic acid amplification cavity to be injected into the gas tail cavity, and the liquid reagent in the liquid cavity stops flowing when reaching a check valve, such that the liquid reagent is injected into the nucleic acid amplification cavity.

6. The microfluidic nucleic acid detection kit according to claim 5, wherein a sample injection port is formed on the kit body, and the sample injection port is in communication with the liquid cavity; a sample injection port is formed at an end of the liquid cavity away from the sample injection flow channel; and a first lyophilized pellet inlet and a first lyophilized pellet outlet are formed in a QC internal standard cavity, and the first lyophilized pellet outlet communicates with the liquid cavity and the QC internal standard cavity.

7. The microfluidic nucleic acid detection kit according to claim 6, wherein the kit body further comprises an upper cover; and the upper cover is provided with a protrusion to seal the sample injection port and the first lyophilized pellet outlet, and the upper cover is configured to cover the first lyophilized pellet inlet.

8. The microfluidic nucleic acid detection kit according to claim 6, wherein an end of the liquid cavity away from the sample injection port is provided with a second sealing membrane, and a puncture needle is configured to be inserted into the liquid cavity such that an end of the puncture needle penetrates through the second sealing membrane and communicates with the liquid cavity; a third sealing membrane is provided at the first lyophilized pellet inlet and a fourth sealing membrane is provided at the first lyophilized pellet outlet;

the fourth sealing membrane comprises a first portion, a second portion, and a third portion, the first portion, the second portion, and the third portion are integrally formed; and the first portion seals the first lyophilized pellet outlet, the second portion seals the liquid cavity, and the third portion is a ring-pull structure and is configured to extend out of the sample injection port.

9. The microfluidic nucleic acid detection kit according to claim 1, wherein a solid reagent required for a nucleic acid amplification is placed in the nucleic acid amplification cavity, and the solid reagent comprises a dry powder reagent, a lyophilized pellet for a reagent, or an internal standard reagent for quality control (QC); and a nucleic acid lysis extract is placed in the liquid cavity with a space reserved for a sample addition, and the nucleic acid lysis extract has a volume of 100 μL to 5,000 μL.

10. The microfluidic nucleic acid detection kit according to claim 9, wherein an end of the sample injection flow channel close to the liquid cavity is provided with a puncture needle; and the puncture needle can-is configured to be inserted into the liquid cavity, such that the puncture needle extends into the liquid cavity to make the sample injection flow channel communicate with the liquid cavity.

11. The microfluidic nucleic acid detection kit according to claim 1, wherein a main flow channel is provided between the nucleic acid amplification cavity and the sample injection flow channel, and a wax column is provided between the sample injection flow channel and the main flow channel.

12. The microfluidic nucleic acid detection kit according to claim 1, wherein the plurality of cavities further comprises a QC internal standard cavity arranged in the kit body, a first lyophilized pellet is placed in the QC internal standard cavity, and the first lyophilized pellet comprises a reagent component required for an internal QC.

13. The microfluidic nucleic acid detection kit according to claim 12, wherein a bottom of the QC internal standard cavity is inclined at a specified angle with a horizontal plane, and a first lyophilized pellet outlet is formed at a lowest position of the bottom of the QC internal standard cavity.

14. The microfluidic nucleic acid detection kit according to claim 1, wherein a second lyophilized pellet or a lyophilized powder is placed in the nucleic acid amplification cavity, and the second lyophilized pellet or the lyophilized powder comprises a reagent component required for a nucleic acid amplification.

15. The microfluidic nucleic acid detection kit according to claim 1, wherein the reagent card is provided with a piston rod, and an end of the piston rod is provided with a rubber piston;

the gas source cavity is shaped like a blind hole on the kit body, the end of the piston rod provided with the rubber piston extends into a blind end of the gas source cavity through an open end of the gas source cavity, and the gas source flow channel is arranged near the blind end of the gas source cavity;

before the kit body slides relative to the reagent card, the rubber piston is located in the gas source cavity at a position lower than the gas source flow channel; and when the kit body slides relative to the reagent card, the rubber piston moves toward the blind end of the gas source cavity to press a gas in the gas source cavity into the liquid cavity.

16. A detection device, comprising the microfluidic nucleic acid detection kit according to claim 1, a first housing, a power module, and a display module, wherein the microfluidic nucleic acid detection kit is removably inserted into the first housing; and the detection device further comprises:

a first heating module configured to heat the nucleic acid amplification cavity; and a first detection module arranged in the first housing and configured to detect a change of an optical signal in the nucleic acid amplification cavity, wherein the optical signal comprises one or more selected from the group consisting of a color signal, a brightness signal, a fluorescence signal, and a saturation signal.

17. The detection device according to claim 16, further comprising: a first circuit board arranged in the first housing and a control unit arranged on the first circuit board, wherein the control unit is electrically connected with the first heating module to control the first heating module to heat the nucleic acid amplification cavity.

18. The detection device according to claim 17, wherein the first heating module comprises a heating member closely surrounding the nucleic acid amplification cavity, a first heating plate arranged at a bottom of the heating member and is-in contact with the heating member for a heat conduction, and a temperature sensor adjacent to the first heating plate; and the temperature sensor is electrically connected with the control unit, and a heat dissipation space is formed between the first heating module and the first circuit board.

19. The detection device according to claim 18, wherein a heating groove, a first hole, and a second holes are formed in the heating member, the first hole and the second hole are arranged oppositely; the first hole and the second hole both penetrate through the heating groove; and the nucleic acid amplification cavity extends into the heating groove and is located between the first hole and the second hole.

20. The detection device according to claim 19, wherein the first detection module comprises a light source and a light sensor, the light source and the light sensor are electrically connected with the first circuit board; the light source and the light sensor both are arranged outside the heating member; and the light source is attached to the first hole and the light sensor is attached to the second hole.

21. The detection device according to claim 20, wherein the first circuit board is provided with a processing unit configured to process and analyze the optical signal acquired by the first detection module and then feed an analysis result back to the display module.

22. The detection device according to claim 21, wherein the processing unit comprises a data acquisition circuit, an analog-to-digital converter (ADC) chip, and a processor; and a signal of the light sensor is acquired by the data acquisition circuit, subjected to an analog-to-digital conversion by the ADC chip, and transmitted to the processor for processing and analysis of a digital signal to obtain detection data.

23. The detection device according to claim 22, wherein the first circuit board is provided with a data communication unit configured to transmit the detection data to a wireless terminal; and the wireless terminal comprises one or more selected from the group consisting of a mobile terminal, a computer, and a network server.

24. The detection device according to claim 23, wherein the first housing comprises a housing body with an opening formed at an upper end and an upper housing cover rotatably connected with the housing body and configured to cover the opening; the nucleic acid detection kit is removably inserted into the opening; and a mounting position for arranging the display module is provided on the housing body, and the display module is arranged at the mounting position.

25. An integrated detection device, comprising the microfluidic nucleic acid detection kit according to claim 1 and a second housing configured to hold the microfluidic nucleic acid detection kit, wherein the integrated detection device further comprises:

a second heating module configured to heat the nucleic acid amplification cavity; and a second detection module arranged in the second housing and configured to detect a change of an optical signal in the nucleic acid amplification cavity, wherein the optical signal comprises one or more selected from the group consisting of a color signal, a brightness signal, a fluorescence signal, and a saturation signal.

26. The integrated detection device according to claim 25, wherein the second housing comprises a front cover and a rear cover removably connected; the front cover and the rear cover cooperate to hold the microfluidic nucleic acid detection kit; and the second detection module is arranged between the front cover and the rear cover.

27. The integrated detection device according to claim 26, further comprising: a second circuit board arranged between the front cover and the rear cover and a control unit arranged on the second circuit board, wherein the control unit is electrically connected with the second heating module to control the second heating module to heat the nucleic acid amplification cavity, and the second circuit board is provided with a second power socket.

28. The integrated detection device according to claim 27, wherein the second heating module comprises a second heating plate closely surrounding the nucleic acid amplification cavity and a temperature sensor arranged on an inner surface of the second heating plate and is-in contact with the reagent card; and the temperature sensor is electrically connected with the control unit.

29. The integrated detection device according to claim 27, wherein the second detection module comprises a light source and a light guide column, the light source and the light guide column are electrically connected with the second circuit board; and the light source and the light guide column are respectively located at two sides of the reagent card.

30. The integrated detection device according to claim 29, wherein the second circuit board is provided with a processing unit configured to process and analyze the optical signal acquired by the second detection module to obtain detection data.

31. The integrated detection device according to claim 30, wherein the processing unit comprises a data acquisition circuit, an ADC chip, and a processor; and a signal of the light sensor is acquired by the data acquisition circuit, subjected to an analog-to-digital conversion by the ADC chip, and transmitted to the processor for processing and analysis of a digital signal to obtain detection data.

32. The integrated detection device according to claim 31, wherein the second circuit board is provided with a data communication unit configured to transmit the detection data to a wireless terminal; and the wireless terminal comprises one or more selected from the group consisting of a mobile terminal, a computer, and a network server.

* * * * *